US010450609B2

United States Patent
Sukumar et al.

(10) Patent No.: US 10,450,609 B2
(45) Date of Patent: Oct. 22, 2019

(54) QUANTITATIVE MULTIPLEX METHYLATION SPECIFIC PCR METHOD—CMETHDNA, REAGENTS, AND ITS USE

(71) Applicant: The Johns Hopkins University, Baltimore, MD (US)

(72) Inventors: Saraswati Sukumar, Columbia, MD (US); Mary Jo Fackler, Hunt Valley, MD (US); Wei Wen Teo, Johor Bahru Johor (MY); Zoila Areli Lopez Bujanda, Bethesda, MD (US); Antonio Wolff, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 709 days.

(21) Appl. No.: 14/402,434

(22) PCT Filed: May 22, 2013

(86) PCT No.: PCT/US2013/042198
§ 371 (c)(1),
(2) Date: Nov. 20, 2014

(87) PCT Pub. No.: WO2013/177265
PCT Pub. Date: Nov. 28, 2013

(65) Prior Publication Data
US 2015/0094222 A1 Apr. 2, 2015

Related U.S. Application Data

(60) Provisional application No. 61/650,083, filed on May 22, 2012.

(51) Int. Cl.
*C12Q 1/6883* (2018.01)
*C12Q 1/686* (2018.01)
*C12Q 1/6886* (2018.01)

(52) U.S. Cl.
CPC .......... *C12Q 1/6883* (2013.01); *C12Q 1/686* (2013.01); *C12Q 1/6886* (2013.01);
(Continued)

(58) Field of Classification Search
None
See application file for complete search history.

(56) References Cited

U.S. PATENT DOCUMENTS 5,639,606 A * 6/1997 Willey ................ B01D 57/02
435/5
8,062,849 B2 * 11/2011 Sukumar ............ C12Q 1/686
435/6.12
(Continued)

FOREIGN PATENT DOCUMENTS

EP        1780292 A1    5/2007
WO    WO 9404706 A1 *  3/1994    ........... C12Q 1/6865
(Continued)

OTHER PUBLICATIONS

Gibson et al. Genome Research 1996; 6: 995-1001.*
(Continued)

*Primary Examiner* — Angela M. Bertagna
(74) *Attorney, Agent, or Firm* — Mintz Levin Cohn Ferris Glovsky and Popeo, P.C.; Peter F. Corless

(57) ABSTRACT

The cMethDNA method of the present invention is a novel modification of the QM-MSP method (U.S. Pat. No. 8,062, 849), specifically intended to quantitatively detect tumor DNA (or other circulating DNAs) in fluids such as serum or plasma at the lowest copy number yet reported. Unique compared to any other PCR-based assay, a small number of copies of a synthetic polynucleotide standard (STDgene) is added to an aliquot of patient serum with standards for a plurality of genes of interest (TARGETgene). Once total DNA is purified PCR is performed wherein the STDgene
(Continued)

and the TARGETgene are co-amplified with the same external primer set, and the amplicons present in a dilution of the first PCR reaction are subjected to real time PCR, and quantified for each gene. Methods of making the STDgene standards and the use of the cMethDNA methods and kits containing the same are disclosed.

11 Claims, 6 Drawing Sheets

Specification includes a Sequence Listing.

(52) U.S. Cl.
CPC .. *C12Q 2600/118* (2013.01); *C12Q 2600/154* (2013.01); *C12Q 2600/16* (2013.01)

(56) References Cited

U.S. PATENT DOCUMENTS

| | | | | |
|---|---|---|---|---|
| 8,822,155 | B2* | 9/2014 | Sukumar | C12Q 1/686 435/6.12 |
| 2002/0086315 | A1* | 7/2002 | Danenberg | C12Q 1/6886 435/6.12 |
| 2005/0239101 | A1 | 10/2005 | Sukumar et al. | |
| 2008/0254470 | A1 | 10/2008 | Berlin | |
| 2009/0136944 | A1 | 5/2009 | Sukumar et al. | |
| 2010/0233703 | A1* | 9/2010 | He | C12Q 1/6886 435/6.12 |

FOREIGN PATENT DOCUMENTS

| | | |
|---|---|---|
| WO | 2005042713 A2 | 5/2005 |
| WO | 2011/132061 A2 | 10/2011 |
| WO | 2012/037128 A2 | 3/2012 |

OTHER PUBLICATIONS

Fackler, et al., "Genome-wide methylation analysis identifies genes specific to breast cancer hormone receptor status and risk of recurrence", Cancer Research (Aug. 8, 2011), vol. 71, No. 19, pp. 6195-6207.
Cohen, Y., et al., "Hypermethylation of CpG island loci of multiple tumor suppressor genes in retinoblastoma", Experimental Eye Research, vol. 86, pp. 201-206, (2007).
Fackler, M., et al., "Genome-wide methylation analysis identifies genes specific to breast cancer hormone receptor status and risk of recurrence" Cancer Research, vol. 71, No. 19, (2011).
Pina-Vazquez, C., et al., "A quantitative competitive PCR method to determine the parasite load in the brain of toxoplasma gondii-infected mice", Parasitology International, vol. 57, No. 3, pp. 347-353, (2008).
Swift-Scanlan, T., "Two-color quantitative multiplex methylation-specific PCR", BioTechniques, vol. 40, No. 2 (2006).
Zimmermann, K., et al., "Technical aspects of quantitative competitive PCR", BioTechniques, vol. 21, No. 2, pp. 268-279, (1996).
Zou, H., et al., "Quantification of methylated markers with a multiplex methylation-specific technology", Clinical Chemistry, vol. 58, No. 2, pp. 375-383 (2011).
Extended European search reported dated Dec. 15, 2015, for related EPO application 13794493.

* cited by examiner

A.

CANCER    NORMAL

B.

C.

FIGURE 2A
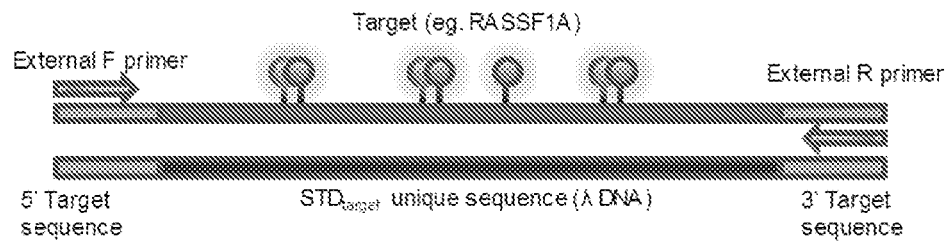
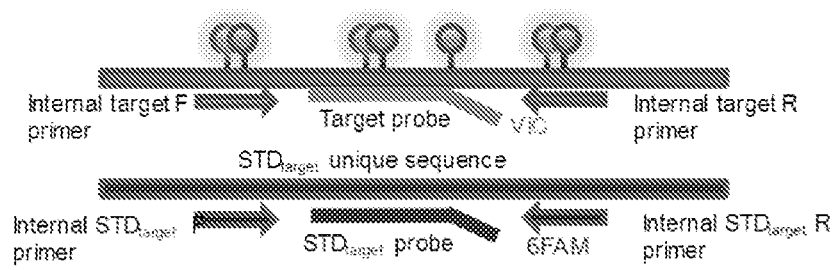
FIGURE 2B
FIGURE 2C
| Verification of array findings using a 10-gene panel | Training Set | |
|---|---|---|
| | Normal | Stage IV |
| Number of samples | 28 | 24 |
| Minimum CMI | 0.01 | 0.01 |
| 25% Percentile | 0.02 | 48.70 |
| Median | 0.04 | 117.30 |
| 75% Percentile | 0.62 | 248.40 |
| Maximum | 7.49 | 616.20 |
| P-value | 0.0001 | |
| Mean | 0.88 | 164.60 |
| Std. Deviation | 1.89 | 154.60 |
| Std. Error | 0.36 | 31.56 |
| Lower 95% CI of mean | 0.14 | 99.28 |
| Upper 95% CI of mean | 1.61 | 229.90 |
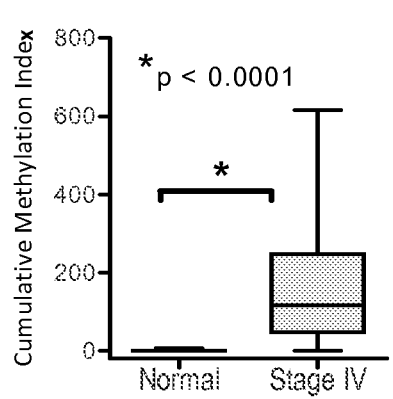

$$\%M = \frac{M}{U+M}(100) \qquad MI = \frac{M}{STD+M}(100)$$

FIGURE 4B

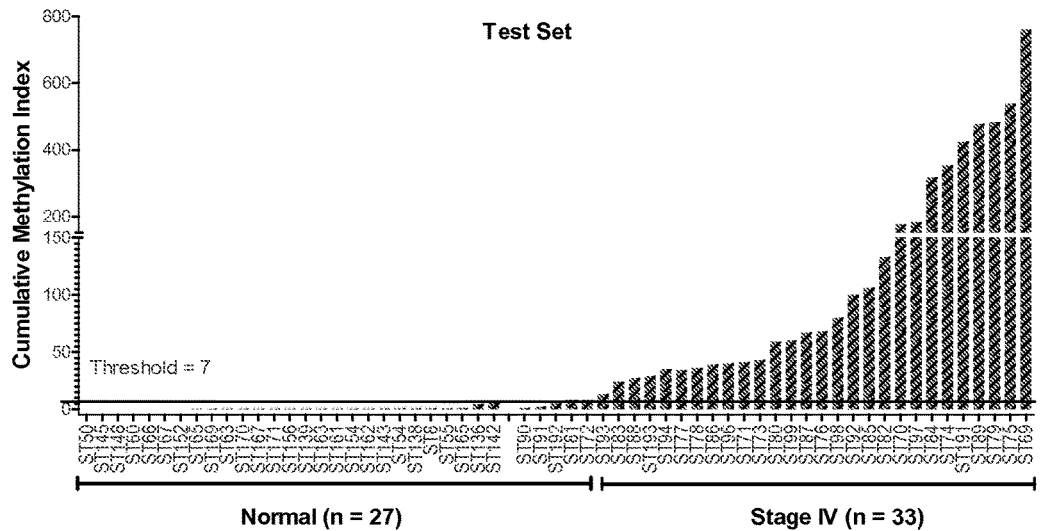

FIGURE 4C

|  | Training Set | Test Set |  | Training Set | Test Set |
|---|---|---|---|---|---|
| ROC Area under the curve | 0.95 | 0.994 | Sensitivity | 92% | 91% |
| 95% confidence interval | 0.874 - 1.027 | 0.984 - 1.005 | Specificity | 96% | 100% |
| P-value | < 0.0001 | < 0.0001 | Likelihood ratio | 25.7 | 24.6 |
| *Positive methylation defined as CMI ≥ 7.0 (set by ROC) | | | Classification Accuracy | 94% | 95% |

FIGURE 4D

| Frequency of Gene Methylation*- cMethDNA | | | | | | | | | | |
|---|---|---|---|---|---|---|---|---|---|---|
|  | AKR1B1 | ARHGEF7 | COL6A2 | GPX7 | HOXB4 | RASGRF2 | RASSF1A | TM6SF1 | TMEFF2 | HIST1H3 |
| Training Set: | | | | | | | | | | |
| Cancer (n = 24) | 15 (63%) | 7 (29%) | 9 (37%) | 5 (21%) | 11 (46%) | 12 (50%) | 18 (75%) | 10 (42%) | 6 (8%) | 12 (50%) |
| Control (n = 28) | 0 | 0 | 1 (4%) | 0 | 0 | 2 (7%) | 1 (4%) | 2 (7%) | 0 | 0 |
| Test Set: | | | | | | | | | | |
| Cancer (n=33) | 14 (42%) | 6 (18%) | 12 (36%) | 10 (30%) | 12 (36%) | 15 (45%) | 22 (67%) | 12 (36%) | 6 (18%) | 18 (55%) |
| Control (n=27) | 0 | 0 | 0 | 0 | 0 | 0 | 0 | 0 | 0 | 2 (7%) |
| *Positive methylation defined as MI > 1 unit | | | | | | | | | | |

Stable/Responsive    Progressive

Stable/Responsive    Progressive

SEQUENCE LISTING

```
<160> NUMBER OF SEQ ID NOS: 240

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gygtaattaa ttagaaggtt tttt                                            24

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aacacctacc ttccaaatac                                                 20

<210> SEQ ID NO 3
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcgcgttaat cgtaggcgtt t                                          21

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cccaatacga tacgacctta ac                                         22

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cgtaccctta aataacccgt aaaatcga                                   28

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tggtgtgtta attgtaggtg tttt                                       24

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccaatacaa tacaacctta acc                                        23

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
acataccttt aaataaccca taaaatcaac                                 30

<210> SEQ ID NO 9
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tttgttgatg ttttgtggaa gtaag                                          25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
attcatcaat actttcaaat aacaca                                         26

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
aaatacatta tcctaccact aacaataca                                      29

<210> SEQ ID NO 12
<211> LENGTH: 216
<212> TYPE: DNA
<213> ORGANISM: Homo sapiens

<400> SEQUENCE: 12
gygtaattaa ttagaaggtt ttttattggt tgttaggtat ttgtattgtt attgtgattg    60
atgattattt ttttgattgt tagatagtgg tgtttttgtt gatgttttgt ggaagtaagt   120
gtattgttag tggtaggata atgtatttga tgtgttattt gaaagtattg atgaatggtg   180
tggtgattta tgatgggtat ttggaaggta ggtgtt                             216

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13 ygttttygagg tgaaggygyg                                               20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctccaacaac ctacaaaaaa c                                              21
```

```
<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gtttttcggg tcgtagcgat g                                              21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caaaaaaccc tccgaatccg aa                                             22

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
aaaccacgta acgatttact cgacga                                         26

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tttgtttttt gggttgtagt gatg                                           24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caaaaaaccc tccaaatcca aata                                           24

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
aataaaccac ataacaattt actcaacaaa                                     30

<210> SEQ ID NO 21
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggaaatgtga ttttgatgtt tatgtt                                            26

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acccaacacc tatttcttaa tcac                                              24

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
acctacacat cactaacaaa catatacaa                                         29

<210> SEQ ID NO 24
<211> LENGTH: 191
<212> TYPE: DNA
<213> ORGANISM: Homo sapiens

<400> SEQUENCE: 24
ygtttygagg tgaaggygyg tgttgatatg ttagtgggtt ggggaaatgt gattttgatg       60
tttatgttta tgtttatatg gtatttggta gatattttgt tgtatatgtt tgttagtgat     120
gtgtaggtta tggtgattaa gaaataggtg ttgggtatta gtgtggtttg gttttttgta     180
ggttgttgga g                                                          191

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aggtttagga gaagttgtag a                                                 21

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
taccaacaat aaaaacccaa ac                                                22
```

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
attcgggttg atagcgattc gt                                            22

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgattccacc aacgccccg                                                19

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
atcccaaaac gaatataaac gacccg                                        26

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gatttgggtt gatagtgatt tgta                                          24

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caattccacc aacaccccaa c                                             21

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
atcccaaaac aaatataaac aacccaac                                      28

```
<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttggtaaggt ggtgatggtg aa                                              22

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcttctacca tcaacaaaca tcc                                             23

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
aactttcacc atacaaataa tcacttcc                                        28

<210> SEQ ID NO 36
<211> LENGTH: 154
<212> TYPE: DNA
<213> ORGANISM: Homo sapiens

<400> SEQUENCE: 36
aggtttagga gaagttgtag atgttttgtg gttgggttag tagtattggt aaggtggtga     60
tggtgaagga agtgattatt tgtatggtga aagttattaa tgtgggatgt ttgttgatgg    120
tagaagattg tagtttgggt ttttattgtt ggta                                154

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggtgaaattg aggtttagag                                                 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atacttctcc aacracacca                                                 20
```

```
<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acggtggtag cggcgtggtt                                                  20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
accccgaata ttaaccgcct ta                                               22

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 41
tactacgcgc aaaccgcaac ccac                                             24

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tgatggtggt agtggtgtgg                                                  20

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
accccaaata ttaaccacct taa                                              23

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
ctactacaca caaaccacaa cccac                                            25

<210> SEQ ID NO 45
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgatagtatt agaagggatt gtag                                            24

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
caaatctaac cacatccaaa ctc                                             23

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
aaatcaccta ccaattcaac catacca                                         27

<210> SEQ ID NO 48
<211> LENGTH: 298
<212> TYPE: DNA
<213> ORGANISM: Homo sapiens

<400> SEQUENCE: 48
ggtgaaattg aggtttagag gatggaggat gatgtaatgt tgatgatagt attagaaggg     60
attgtaggag gagtttggta tggttgaatt ggtaggtgat ttggttgttg atttgagttt    120
ggatgtggtt agatttgatg agtagatggt tagagttagg tgttattttt ttggtatgga   180
aagtgatgtg aaaaaaatag tggtagttgt tgaatagttg ttgagttgat aggtgttggt   240
tgtatagaaa gtggggattt ttgttgggta gtataaagtg gtgttgttgg agaagtat    298

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtgtgtgttt ttattgtaaa tgg                                             23

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
```
ataaaatttc ttcacrccac c                                         21

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcgtacgaag taaatagttc gtaa                                      24

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
taaccgaaac gctcttacga ac                                        22

<210> SEQ ID NO 53
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 53
tacttacgcg aaactttacc gccga                                     25

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tttgtatgaa gtaaatagtt tgtaag                                    26

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aataaccaaa acactcttac aaact                                     25

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 56
aactacttac acaaaacttt accaccaa                                  28

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gatttagagt tggatgtgtg gat                                              23

<210> SEQ ID NO 58
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
accaccatac taataatcaa atcta                                            25

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
aaatatcact catcaccaaa taaatccaa                                        29

<210> SEQ ID NO 60
<211> LENGTH: 140
<212> TYPE: DNA
<213> ORGANISM: Homo sapiens

<400> SEQUENCE: 60
gtgtgtgttt ttattgtaaa tggtggattt agagttggat gtgtggatgg agttttggat      60
ttatttggtg atgagtgata ttttggtatt gttagatttg attattagta tggtggttag     120
gtggtgtgaa gaaattttat                                                 140

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ttagaggyga gagagtagtt                                                  20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aaactactac taaccrcctc                                                  20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 63
cgggattttg ggttttcgtc g                                             21

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 64
cgacgaataa cgacgcaaaa ac                                            22

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 65
aaccgaacga taacgaaaac gacgaa                                        26

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 66
gttgggattt tgggtttttg ttg                                           23

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 67
caacaaataa caacacaaaa accc                                          24

<210> SEQ ID NO 68
<211> LENGTH: 32
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 68
aacaataaca aaacaacaa aaataataac aa                                  32

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gttagttttg tagtgtattg agtat                                          25

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
catcttccac aataaacttc caatt                                          25

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 71
taactccacc tattctacct accattt                                        27

<210> SEQ ID NO 72
<211> LENGTH: 228
<212> TYPE: DNA
<213> ORGANISM: Homo sapiens

<400> SEQUENCE: 72
ttagaggyga gagagtagtt atataatggt gtgattgtta tgttttttga attgttagtt    60
ttgtagtgta ttgagtattt tgttttgatg aaatggtagg tagaataggt ggagttagat   120
agtaattgga agtttattgt ggaagatgtt attagaattg gtgtgttttt ggtggtgatg   180
tttttgtggt ataattattt gtagaagaga ggtggttagt agtagttt                228

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gatttatagt ttttagtttt gga                                            23

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aaaccactaa acaaaatact ac                                            22

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tttcgcggag ttagcgagag                                               20

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
aaaccataac gacgtactaa cg                                            22

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 77
aaaacgaaac gaacgccgct caaac                                         25

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gttttgtgga gttagtgaga gg                                            22

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
aaaccataac aacatactaa catc                                          24

<210> SEQ ID NO 80
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
cttaaaacaa aacaaacacc actcaaac                                      28

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gtgtgggatg tgtttagtga ttt                                          23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
caatcctaca caaacatcaa cat                                          23

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
ggtgatgtgt tgtatgttgg tatgg                                        25

<210> SEQ ID NO 84
<211> LENGTH: 317
<212> TYPE: DNA
<213> ORGANISM: Homo sapiens

<400> SEQUENCE: 84
gatttatagt ttttagtttt ggatgtggtg gatgtggata aatgggtgtt gtatgttatt    60
ggttagtatt gtgattagtt agtgttggat ggttttggtg gtatggagtt gtgtattatt   120
tgtaatgtgt atttgattat atagtgtaag gtgtgggatg tgtttagtga ttttttgtttg   180 gtgatgtgtt gtatgttggt atggaatggg tagatgttga tgtttgtgta ggattgattg   240
ttggataaga tgtggattta taattgtagt aatgtggtga tgttggatga tggtggtagt   300
attttgttta gtggttt                                                 317

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gagggagtta gttgggttat                                              20

<210> SEQ ID NO 86
<211> LENGTH: 20
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 86
cctccaaaaa atacataccc                                                   20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gtaagaagac ggtcgaggcg                                                   20

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
acaactctac tcgccctcga a                                                 21

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
aacgaaccac ttctcgtacc aacga                                             25

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gagtaagaag atggttgagg tg                                                22

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
caacaactct actcaccctc aa                                                22

<210> SEQ ID NO 92
<211> LENGTH: 27
<212> TYPE: DNA
<213> ORGANISM: Artificial Sequence
<220> FEATURE:
<223> OTHER INFORMATION: Description of Artificial Sequence: Synthetic
``` probe

<400> SEQUENCE: 92
aaacaaacca cttctcatac caacaac                               27

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
tgtatgagtt tgtggtgaat aatg                                  24

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
aactcaccat caaacacttt ccc                                   23

<210> SEQ ID NO 95
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 95
tacaaaccca acatcctcta tctattc                               27

<210> SEQ ID NO 96
<211> LENGTH: 284
<212> TYPE: DNA
<213> ORGANISM: Homo sapiens

<400> SEQUENCE: 96
gagggagtta gttgggttat taggaagtgt ttattatttg gtttatggag gtaattttt      60 atgttgaaaa tgtggtgtat tggttgtttg gtatgtatga gtttgtggtg aataatgttt   120
ttgaatagat agaggatgtt gggtttgtag agtttgtttt tgtgggaaag tgtttgatgg   180
tgagttgagt tttgttttga aattggtgtg tgagatgggg tgatttgatt ggtgtgttat   240
gtttgttggg atgttattta tggagggtat gtattttttg gagg                    284

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gttttatagt ttttgtattt agg                                   23

<210> SEQ ID NO 98
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
aactcaataa actcaaactc cc                                              22

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gcgttgaagt cggggttc                                                   18

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cccgtacttc gctaacttta aacg                                            24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 101
acaaacgcga accgaacgaa acca                                            24

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ggtgttgaag ttggggtttg                                                 20

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cccatacttc actaacttta aac                                             23

<210> SEQ ID NO 104
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      probe

<400> SEQUENCE: 104
ctaacaaaca caaaccaaac aaaacca                                        27

<210> SEQ ID NO 105
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ttagggtaga ttgtggatat tag                                            23

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
atactaacaa ctatccaata caac                                           24

<210> SEQ ID NO 107
<211> LENGTH: 33
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 107
aggttgaaat tagtatgtgt tattttggta tgg                                 33

<210> SEQ ID NO 108
<211> LENGTH: 206
<212> TYPE: DNA
<213> ORGANISM: Homo sapiens

<400> SEQUENCE: 108
tagaattcgt tttatagttt ttgtatttag ggtagattgt ggatattaga taggttgaaa    60
ttagtatgtg ttattttggt atggtgttgt attggatagt tgttagtatt aatattaaat   120
tgggttatga ttattatttt tatatttgta gtgtgaatat tgttggtaaa ttggtatttg   180
tggagggagt ttgagtttat tgagtt                                       206

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
aggagatatt gttgagggga                                                20

<210> SEQ ID NO 110
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tcactcatac taaaccrcca a                                              21

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cgtttagcgg gatgcggtga                                                20

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
acacgaaaac cccgataacc g                                              21

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 113
aaacactcat cgcaaccgcc gcg                                            23

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
tgtttagtgg gatgtggtga ag                                             22

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
acacaaaaac cccaataacc aca                                            23

<210> SEQ ID NO 116
<211> LENGTH: 25
```

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 116
aaacactcat cacaaccacc acacc                                           25

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
ttagatgttg attggttgtg tttg                                            24

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
atcatcataa aactcaacaa tcaatt                                          26

<210> SEQ ID NO 119
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 119
ccaaacatca aatctttaac ttttaccaa                                       29

<210> SEQ ID NO 120
<211> LENGTH: 253
<212> TYPE: DNA
<213> ORGANISM: Homo sapiens

<400> SEQUENCE: 120
aggagataty gttgagggga gaggatgtta tgtttgtatt aaattttata atgttggtga     60
aaggtgttgg gattattttg tgggtttata aggggagtgg tgattttat gtgaatttgt    120 ttttagatgt tgattggttg tgtttggtaa aagttaaaga tttgatgttt ggtgaattga    180
ttgttgagtt ttatgatgat agttattttg atgatgaaga tgtagattgg atttggtggt    240
ttagtatgag tga                                                       253

<210> SEQ ID NO 121
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ttatggtagt agtttttygy gtt                                             23
```

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
cccacaacac cataactaat tc                                              22

<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tttcgtttcg gggttgagtt tag                                             23

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
acgataacaa taacacccga cga                                             23

<210> SEQ ID NO 125
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 125
caaacccgcg cataatctcg aaaatt                                          26

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ttttgttttg gggttgagtt tagtt                                           25

<210> SEQ ID NO 127
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
caacaataac aataacaccc aacaa                                           25

```
<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 128
caaacccaca cataatctca aaaatttc                                          28

<210> SEQ ID NO 129
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
attagtgaag ggttgattga agg                                               23

<210> SEQ ID NO 130
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ccaaatatat taatattccc ctcaa                                             25

<210> SEQ ID NO 131
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 131
accaacatac tattcaacaa cacacttt                                          28

<210> SEQ ID NO 132
<211> LENGTH: 276
<212> TYPE: DNA
<213> ORGANISM: Homo sapiens

<400> SEQUENCE: 132
ttatggtagt agtttttygy gttatgggta aaggaagtag taagggtat attttgtgtg        60 aagtgaagga taatttgaag tttatgtagt tgttgagtgt gattgatgtt attagtgaag      120
ggttgattga aggtttggtg gatggtttaa aaagtgtgtt gttgaatagt atgttggtgt      180
tggatattga ggggaatatt aatatatttg gtgttatggt ggtgttttgg gttggtgagt      240
aggagtagat tttggaatta gttatggtgt tgtggg                                276

<210> SEQ ID NO 133
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 133
gagatgagat attatttatt gtg                                          23

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
cctcccaaac cattcaaaaa c                                            21

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gttagggttc gggggcgttg tt                                           22

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ccgtcgcctt cctccgacga a                                            21

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 137
aaacgatttc cttccccgcc gaaa                                         24

<210> SEQ ID NO 138
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ttagggtttg ggggtgttgt ttgtatg                                      27

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139

```
ccatcacctt cctccaacaa ac                                              22
```

<210> SEQ ID NO 140
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 140

```
aaacaatttc cttccccacc aaaaca                                          26
```

<210> SEQ ID NO 141
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141

```
ttgtatttat tgatttggta aatggg                                          26
```

<210> SEQ ID NO 142
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142

```
acatcattca taaatatcta attacc                                          26
```

<210> SEQ ID NO 143
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 143

```
acaccacaaa catcaacatt tcattccc                                        28
```

<210> SEQ ID NO 144
<211> LENGTH: 273
<212> TYPE: DNA
<213> ORGANISM: Homo sapiens

<400> SEQUENCE: 144

```
gagatgagat attatttatt gtgatatgga ggaaggtaaa ttgagttagt ttttggttgt      60
tgttaattgt attgtattta ttgatttggt aaatgggaat gaaatgttga tgtttgtggt    120
gtagggtaat tagatattta tgaatgatgt gtttttgaag tgtttgatgg ttttttattat   180 tattagtggt ggtaattttt tggtttttttt ttgatattgg atggaaagtt gattgttaaa   240
aatgtggata ttgtttttga atggtttggg agg                                 273
```

<210> SEQ ID NO 145
<211> LENGTH: 22
<212> TYPE: DNA
<213> ORGANISM: Artificial Sequence
<220> FEATURE:

<223> OTHER INFORMATION: Description of Artificial Sequence: Synthetic
    primer

<400> SEQUENCE: 145
agtaaagygt ttgtaggtaa at                                              22

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 146
tttctccctc cctacctaat                                                 20

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 147
cgtgcgtttg gagaggattt c                                               21

<210> SEQ ID NO 148
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 148
cgatcctaca ttttcgatta cga                                             23

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 149
aacgctaacg actcaccgct actat                                           25

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 150
atgtgtgttt ggagaggatt ttg                                             23

<210> SEQ ID NO 151
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
accaatccta cattttcaat tacaa                                           25

<210> SEQ ID NO 152
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
taaaacacta acaactcacc actactat                                        28

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
gagggtgtaa ttgataagag tttt                                            24

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
cctacaacaa caccattcac aat                                             23

<210> SEQ ID NO 155
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
atcataccac taaccaacac aataactt                                        28

<210> SEQ ID NO 156
<211> LENGTH: 191
<212> TYPE: DNA
<213> ORGANISM: Homo sapiens

<400> SEQUENCE: 156
agtaaagygt ttgtaggtaa ataggtaga gtattatgtt gattgtggtt ttttagttgg      60
agggtgtaat tgataagagt ttttgtgtgg tgtttgtgga taaaataaaa gttattgtgt    120
tggttagtgg tatgattatt attgtgaatg gtgttgttgt aggtaaggtt aattaggtag    180
ggagggagaa a                                                        191

<210> SEQ ID NO 157
<211> LENGTH: 21
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 157
ggatttgtta gttttaggga a                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
acacaatatt acaaaccacc a                                              21

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
aaagcggagt tcgttcgttt ttt                                            23

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ctacctccaa ccgccgaaaa c                                              21

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161
accctctcga ctcatcctcc gac                                            23

<210> SEQ ID NO 162
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
aaagtggagt ttgtttgttt tttatt                                         26

<210> SEQ ID NO 163
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 163
ctacctccaa ccaccaaaaa cc                                              22

<210> SEQ ID NO 164
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
aaccctctca actcatcctc caact                                           25

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tgggttgatg tatattgtgt ttag                                            24

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
aacctcacac caattcaaca aac                                             23

<210> SEQ ID NO 167
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
aaatccaaca aatacatatc caaatcact                                       29

<210> SEQ ID NO 168
<211> LENGTH: 246
<212> TYPE: DNA
<213> ORGANISM: Homo sapiens

<400> SEQUENCE: 168
ggatttgtta gttttaggga atgggttgat gtatattgtg tttagtttgt ttttagtga      60 tttggatatg tatttgttgg attttagttt gttgaattgg tgtgaggttg atgaagagtt    120
tgaagatgat gtgttgatgt agaaagtggt agggtttgtt ggaggtgttt gttttggttt    180
ggatgggaat gaagttattt tgttttttt ggatgtggtg gatattggtg gtttgtaata    240
ttgtgt                                                              246

<210> SEQ ID NO 169
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
tttaggggtt tttaaggtag g                                               21

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
aaaaacccta tacctccctc                                                 20

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ggtatcgtac ggttcgggaa a                                               21

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
aacgaaaccg aacgcgaaat cc                                              22

<210> SEQ ID NO 173
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 173
atcctacctc gcctatccga aataaaca                                        28

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ttgggtattg tatggtttgg gaa                                             23

<210> SEQ ID NO 175
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
aaacaaaacc aaacacaaaa tccc                                          24

<210> SEQ ID NO 176
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 176
tcctacctca cctatccaaa ataaaca                                       27

<210> SEQ ID NO 177
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
ttgttagtgg tgtagtattt gattg                                         25

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
accttcaata tatcccatca cac                                           23

<210> SEQ ID NO 179
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 179
aatattcccc actatctaca ataacttc                                      28

<210> SEQ ID NO 180
<211> LENGTH: 223
<212> TYPE: DNA
<213> ORGANISM: Homo sapiens

<400> SEQUENCE: 180 tttagggtt tttaaggtag gagagtggta tggtgaatgg tgttatgttg ttagtggtgt    60
agtatttgat tgtagaagtt attgtagata gtggggaata ttaggtgttg gtgtgatggg  120
atatattgaa ggtggtgaag ggtgtgagtt ttttgttttg tttgattgta atagtggatg  180
atggtagtga gtggttggtt agtgagggag gtataggggtt ttt                    223
```

<210> SEQ ID NO 181
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gtaagggttg tttttygggg                                              20

<210> SEQ ID NO 182
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
aaccctatac cccttctcc                                               19

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
taggtacgcg agcgtatcga g                                            21

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ccgacgaact acgtacaatt ac                                           22

<210> SEQ ID NO 185
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 185
tcgtagtttc ggttttata gtttcggt                                      28

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
taataggtat gtgagtgtat tgag                                         24

<210> SEQ ID NO 187

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
ttcccaacaa actacataca attac                                          25

<210> SEQ ID NO 188
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 188
ttgtagtttt ggtttttata gttttggt                                       28

<210> SEQ ID NO 189
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
atgtagattg tggattttag tgttg                                          25

<210> SEQ ID NO 190
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
ataccaacat aatcatcatc acaaat                                         26

<210> SEQ ID NO 191
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 191
ttttgttatg tattgggtga tgttattga                                      29

<210> SEQ ID NO 192
<211> LENGTH: 290
<212> TYPE: DNA
<213> ORGANISM: Homo sapiens

<400> SEQUENCE: 192
gtaagggttg tttttygggg tgtggttgat taaaatagaa ttgttggaaa tgtagattgt    60 ggatttagt gttggtgtag aagggttttg ttatgtattg ggtgatgtta ttgaaatttg   120
tgatgatgat tatgttggta ttagtattgg tggttgtgtg ttggtggcga atagttagat  180
ttggatgttg atgtttgatt gtgaaattat gttgttattt tttggtattg tgttgataag   240
```

-continued tttggttgat ggaagtggta atttggttag tggagaaggg gtatagggtt      290

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
tgggaaagag ggaaaggttt      20

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
tactcactaa taacraaaac tac      23

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
cggtcggcgt cgtgatttag      20

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
aactccaacg aaaacctcgc g      21

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 197
aaaataatcc cgccccgctc cgc      23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
gtggttggtg ttgtgattta gta      23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
aactccaaca aaaacctcac aac                                              23

<210> SEQ ID NO 200
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 200
aaaaataatc ccaccccact ccacc                                            25

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ggtgttgttg attatggtgt ttaa                                             24

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tactacaaca cataacccaa ctc                                              23

<210> SEQ ID NO 203
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 203
aacattcaca ccatatccac tcaatatt                                         28

<210> SEQ ID NO 204
<211> LENGTH: 257
<212> TYPE: DNA
<213> ORGANISM: Homo sapiens

<400> SEQUENCE: 204
tgggaaagag ggaaaggttt gtggtatgtt atgtagtgtg tggttgggaa aaattgttat      60
tttattgatg tggtgaaaat tttgatggtg gtgttgttga ttatggtgtt taaataaaat     120
attgagtgga tatggtgtga atgttttttg aaagagttgg gttatgtgtt gtagtattaa     180

-continued ttgaggatgg taataaagtg atgaaatata ttgaattttg tgtagttgta ttgggtagtt     240
tttgttatta gtgagta     257

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
aaactacaaa acaaaaccac     20

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
gtttgttaag aggaagtttt     20

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
tagggaaggg ggtacgggtt t     21

<210> SEQ ID NO 208
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
cgctcacgac cgtaccctaa     20

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 209
acttcctact acgaccgacg aacc     24

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 210
aagtttttga ggtttgggta ggga                                         24

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
accaacctca cccacactcc ta                                           22

<210> SEQ ID NO 212
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 212
caacttccta ctacaaccaa caaacc                                       26

<210> SEQ ID NO 213
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
ataatgttag tagattggag gagtt                                        25

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
aacccacata acattccact tatc                                         24

<210> SEQ ID NO 215
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 215
aaagagtggg aggatgttag tgataagtg                                    29

<210> SEQ ID NO 216
<211> LENGTH: 262
<212> TYPE: DNA
<213> ORGANISM: Homo sapiens

<400> SEQUENCE: 216
gtttgttaag aggaagtttt gtgagtgatg atgtggaagg ttatttggat ttttttaaag   60
```

```
gtaagataat tgaattttat tttggtaagg agttgttgga aaaagttgag ttgatggagg      120
ataatgttag tagattggag gagtttttga aagagtggga ggatgttagt gataagtgga      180
atgttatgtg ggttgttaaa attgagtaga ttaaagatgg taaatattat gttgtgggta      240
ttgtggtttt gttttgtagt tt                                               262
```

<210> SEQ ID NO 217
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217

```
tttagttgag ggaaggggaa                                                   20
```

<210> SEQ ID NO 218
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218

```
aactacaaca caactacct aa                                                 22
```

<210> SEQ ID NO 219
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219

```
ggttaggcgg ttagggcgtc                                                   20
```

<210> SEQ ID NO 220
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220

```
ccgaacgcct ccatcgtatc                                                   20
```

<210> SEQ ID NO 221
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 221

```
cacacaccga ccgaataaaa accgt                                             25
```

<210> SEQ ID NO 222
<211> LENGTH: 21
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 222
gggttaggtg gttagggtgt t                                          21

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
taaccaaaca cctccatcat atc                                        23

<210> SEQ ID NO 224
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 224
aaacacacac caaccaaata aaaaccat                                   28

<210> SEQ ID NO 225
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ggaattggat tgatttgaat aatgg                                      25

<210> SEQ ID NO 226
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
aaaacatcca tcttcataac attac                                      25

<210> SEQ ID NO 227
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 227
ataacaaaca ataacctaca tatcttcaac                                 30

<210> SEQ ID NO 228
<211> LENGTH: 173
<212> TYPE: DNA
<213> ORGANISM: Homo sapiens

<400> SEQUENCE: 228

-continued

```
tttagttgag ggaaggggaa ttggattgat ttgaataatg gttgggagat ggtgatagag    60
tttgttgaag atatgtaggt tattgtttgt tatggttgta atgttatgaa gatggatgtt   120
tttggttgta ttagttgggg gtaggtatat tttaggtagt tgttgttgta gtt          173
```

<210> SEQ ID NO 229
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229

```
gtatagagga atttaaagtg tg                                             22
```

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230

```
tctttcctat ttctcacctt aa                                             22
```

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231

```
ggcgtaggcg gaatatcgtt t                                              21
```

<210> SEQ ID NO 232
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232

```
aaaccgaaac gctactccta ac                                             22
```

<210> SEQ ID NO 233
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 233

```
acgccttttt atttacgacg acttaac                                        27
```

<210> SEQ ID NO 234
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 234
tgggtgtagg tggaatattg ttt                                              23

<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
aaccaaaaca ctactcctaa ctc                                              23

<210> SEQ ID NO 236
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 236
tttacacctt tttatttaca acaacttaac                                       30

<210> SEQ ID NO 237
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
gttgtaatgg ttattaattg tgttg                                            25

<210> SEQ ID NO 238
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
ccctttcctt taccaatttc ca                                               22

<210> SEQ ID NO 239
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 239
atctcacaaa caacctataa caccaac                                          27

<210> SEQ ID NO 240
<211> LENGTH: 222
<212> TYPE: DNA
<213> ORGANISM: Homo sapiens

<400> SEQUENCE: 240

```
gtatagagga atttaaagtg tgattagtaa aatggtggtg tttggtgttg ttgtaatggt        60
tattaattgt gttgttttat ttgtgatatt gtagttggtg ttataggttg tttgtgagat       120
aaaggtatgt tggaaattgg taaaggaaag ggttaggttg aaaagggtta tggttaaaaa       180
tttgtaggtt agaattaaag ttaaggtgag aaataggaaa ga                          222
```

QUANTITATIVE MULTIPLEX METHYLATION SPECIFIC PCR METHOD—CMETHDNA, REAGENTS, AND ITS USE

CROSS-REFERENCE TO RELATED APPLICATIONS

This application is a 35 U.S.C. § 371 U.S. national entry of International Application PCT/US2013/042198, having an international filing date of May 22, 2013, which claims the benefit of U.S. Provisional Application No. 61/650,083, filed May 22, 2012, the content of each of the aforementioned applications is herein incorporated by reference in their entirety.

GOVERNMENT SUPPORT

This invention was made with government support under grant nos. CA006973 and W81XWH-04-1-0595, awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on May 13, 2013, is named P12014-02_SL.txt and is 58,416 bytes in size.

BACKGROUND OF THE INVENTION

It is now clear that epigenetic alterations including hypermethylation of gene promoters and some regions internal to a gene are consistent and early events in neoplastic progression. Such alterations are thought to contribute to the neoplastic process by transcriptional silencing of tumor suppressor gene expression, and by increasing the rate of genetic mutation. DNA methylation is reversible, since it does not alter the DNA sequence; however, it is heritable from cell to cell. As such, methylated genes could serve as biomarkers such as for early detection of cancer, risk assessment, predicting and monitoring response to therapy, and early detection of relapse.

Tumor DNA can be found in various body fluids and these fluids can potentially serve as diagnostic material. Evaluation of tumor DNA in these fluids requires methods that are specific as well as sensitive. A PCR-based technique called methylation-specific PCR (MSP) is known to detect one copy of methylated genomic DNA in one-thousand unmethylated copies of genomic DNA. Quantitative real time PCR (Q-PCR) allows a highly sensitive quantification of transcriptional levels or levels of the DNA of the gene of interest in a few hours with minimal handling the samples. cDNA or genomic copies of the gene of interest are quantitated by detecting PCR products as they accumulate using an optically detectable polynucleotide probe. Quantitative MSP (Q-MSP) allows highly sensitive detection of gene promoter methylation levels by real time PCR with methylation-specific primers probes.

Quantitative and multiplex MSP techniques have been modified in order to co-amplify several genes simultaneously in a nested or multiplex MSP assay to develop quantitative multiplex methylation-specific PCR (QM-MSP). The QM-MSP method is based on real-time PCR that uses one or more distinguishable optically detectable probes to increase the assay specificity and the sensitivity such that one to ten copies of the desired methylated gene among 100,000 unmethylated copies of the gene can be detected.

Studies from the inventors have shown that a panel of methylation markers can detect 100% of all breast carcinomas and 95% of DCIS, and cancer in cells from ductal fluid and in spontaneous nipple discharge. However, reproducible detection of methylated DNA from serum/plasma proved to be more difficult. Many studies in the past 15 years have reported the use of a single or a panel of markers to detect breast cancer in serum/plasma. However, no clinical validation studies have followed these preliminary findings, suggesting that there were technical difficulties, yet to be resolved, in this analysis: 1) First, the amount of methylated tumor DNA shed in the serum is a very small fraction of the total unmethylated DNA (either matching gene-specific DNA or a reference DNA such as actin) shed by normal cells. There is a disproportion between the relative abundance of the unmethylated or reference DNA and the rarity of the target methylated DNA in body fluids. This leads to lack of robustness of the assay due to masking of methylated signals by the more abundant species; 2) The extent of shedding of normal unmethylated DNA fluctuates daily and with various clinical states, such as surgery or infection; if the reference fluctuates, then inaccuracies occur in interpretation of % methylation of a target gene of interest; 3) The most sensitive assays available utilize nested PCR (with or without multiplex) to pre-amplify amplicons of target and reference DNA using external primers outside the region of interest prior to round two quantitative PCR. But there are technical limitations such that the target and reference DNA regions need to be co-amplified in the pre-amplification PCR reaction with the same efficiency, ideally using the same pair of external primers in order to maintain the accurate starting ratio of target to reference DNA. In nested PCR Actin or other genes cannot accurately serve as a reference for the gene of interest because of differences in efficiencies of primer hybridization between the non-identical genes. Thus the ratio of target to reference changes with each cycle of pre-amplification, depending on the relative differences in efficiency of hybridization of the DNA-specific primers to the target and reference DNAs; 4) Existing serum MSP assays usually require 10-20 ng genomic DNA per assay to test one gene one time. Since the level of total DNA in serum of cancer patients is low [median 65.4 ng/ml; range 6.3-268.6 ng/ml; Holdenrieder et al., Ann. N.Y. Acad. Sci. 1137:162-170 (2008)] assays of several genes require a significant amount of serum, making repeat studies problematic and clinical validation difficult because archival sera from existing clinical studies are available only in small volumes.

SUMMARY OF THE INVENTION

To overcome these problems the inventors have now developed a novel quantitative multiplex methylation specific PCR method which is termed "cMethDNA." This method overcomes all limitations discussed above: 1) For every gene marker, a recombinantly engineered gene-specific standard (STDgene) was developed to act as reference DNA. To avoid masking of the target DNA (TARGETgene) only 50 copies (genomic equivalent of 150 pg) of reference per 300 µl of serum is used; 2) Unmethylated or irrelevant DNA is not assayed therefore fluctuations in unmethylated DNA will not affect quantitation of methylation of the gene target; 3) Each STDgene DNA is designed with 5' and 3' ends (~20-22 bases per end) homologous to the methylated TARGETgene of interest, and to have a similar number of intervening nucleotides between ends so during pre-amplification PCR (round one), both TARGETgene and STDgene DNAs can be co-amplified with a single set of external primers independent of the methylation status of the TARGETgene; and 4) Using input genomic DNA (as low as 1.9 ng) isolated from 300 μl of serum [median 65.4 ng/ml; range 6.3-268.6 ng/ml; Holdenrieder et al., Ann. N.Y. Acad. Sci. 1137:162-170 (2008)], multiplex PCR is performed during the pre-amplification step to facilitate synthesis of hundreds of millions of amplicons of up to 12 or more TARGETgene DNAs (and their respective STDgene DNAs). Taken together, cumulative and individual TARGETgene methylation is expressed as the cumulative methylation index (CMI), for the marker panel, and the methylation index (MI) for individual genes. CMI is calculated by determining the sum of the MI for individual genes the panel. MI=[#copies TARGETgene/#copies (TARGETgene+STDgene)](100).

In accordance with one or more embodiments, the present inventors developed the cMethDNA assay, that, using a panel of selected TARGETgenes, discovered through whole genome methylation array analysis, detects methylated TARGETgene DNA in training and test sets of Stage 4 patient sera (57 cancer, 55 normal) with a sensitivity >90% and specificity >96%. A striking concordance of DNA methylation patterns was observed between the primary, distant metastases and serum from the same patient from three different cohorts-Stage 4 at diagnosis, recurrent metastatic breast cancer, and samples collected at autopsy, suggesting that a core methylation signature is retained over time. Methylation levels appeared to correlate with chemotherapeutic response post treatment. In a pilot study of 29 patients, it is shown that cMethDNA is capable of monitoring response to therapy. Together, the data in the following examples shows that the cMethDNA methods of the present invention: 1) can detect tumor DNA shed into blood, 2) reflect the methylation alterations typical of the primary tumor and its metastatic lesions, and 3) shows potential to evaluate response to treatment after chemotherapeutic interventions.

The cMethDNA methods of the present invention are a novel modification of the QM-MSP method (U.S. Pat. No. 8,062,849), and incorporated by reference herein in its entirety) specifically intended to quantitatively detect tumor DNA (or other circulating DNAs) in fluids such as serum or plasma at the lowest concentration (50 copies in 300 μl serum) yet reported. Unique compared to any other PCR-based assay, a small number of copies of a synthetic polynucleotide standard (the STDgene) is added to an aliquot of patient serum. In a standard procedure, a cocktail of standards for a plurality of genes of interest (TARGETgenes) is added to a sample of serum. Once total DNA is purified and processed, a PCR (pre-amplification, multiplex step) is performed wherein the STDgene and TARGETgene are co-amplified with the same external primer set in a manner independent of the methylation status of the TARGETgene. In the second step of nested PCR, amplicons present in a dilution of the first PCR reaction are subjected to real time PCR, and quantified for each gene in one or two well(s) by two-color real-time PCR. Products are calculated by absolute quantitation with internal primer sets specific for the methylated TARGETgene and associated STDgene. The methylation index of each gene (MI), as well as the cumulative methylation (CMI) of the gene panel is then determined based on copy number.

In accordance with an embodiment, the present invention provides a method of quantifying the methylation of one or more genes of interest in a sample from a subject comprising: a) adding to the sample containing DNA from the subject, a plurality of copies of STDgene specific for each TARGETgene of interest being detected; b) isolating and processing the DNA in the sample, c) preparing the DNA in (a) for methylation specific PCR; d) amplifying the DNA in (b) with one or more pairs of external methylation-independent PCR primers, where each single primer pair is capable of selectively hybridizing to only one of the TARGETgenes being detected and as well as the STDgene specific for that TARGETgene, using PCR under conditions sufficient to produce a first amplification product; e) obtaining a diluted sample of the first amplification product of (d); f) adding to (e) one pair of internal methylation-dependent PCR primers specific for each TARGETgene, and one pair of internal PCR primers specific for each STDgene for the gene of interest, one or more optically detectable labeled DNA probes which specifically hybridize to a target sequence of each of TARGETgene, and one or more optically detectable labeled DNA probes which specifically hybridize to each STDgene; and g) amplifying the DNA in (f) using quantitative RT-PCR under conditions sufficient to produce a second amplification product which provides quantification of the amount of copies of each methylated TARGETgene and the amount of copies of each STDgene.

In accordance with another embodiment, the present invention provides a method of diagnosing the development of a disease associated with aberrant DNA methylation in a sample from a subject comprising: a) adding to the sample containing DNA from the subject, a plurality of copies of a STDgene for each TARGETgene of interest being detected; b) isolating and processing the DNA in the sample of (a) to prepare the DNA for methylation specific PCR; c) amplifying the DNA in (b) with one or more pairs of external methylation-independent PCR primers, where each single primer pair is capable of selectively hybridizing to only one of the TARGETgenes of interest being detected and the STDgene specific for that same gene, using PCR under conditions sufficient to produce a first amplification product; d) obtaining a diluted sample of the first amplification product of (c); e) adding to (d) one pair of internal methylation-dependent PCR primers specific for each TARGETgene, and one pair of internal PCR primers specific for each STDgene for the TARGETgene, one or more optically detectable labeled DNA probes which specifically hybridize to each TARGETgene of the gene of interest, and one or more optically detectable labeled DNA probes which specifically hybridize to each STDgene for the gene of interest; and f) amplifying the DNA in (e) using quantitative RT-PCR under conditions sufficient to produce a second amplification product which provides quantification of the amount of copies of each methylated TARGETgene and the amount of copies of each STDgene of the gene of interest, wherein an increase in the quantity of methylated copies of the one or more TARGETgenes obtained from the sample compared to control is indicative of an increased risk and/or presence of the disease; and b) diagnosing the subject as having an increased risk and/or presence of the disease.

In accordance with a further embodiment, the present invention provides a STDgene for use in RT-PCR comprising an oligonucleotide having 5' and 3' end nucleotide sequences which are identical to the 5' and 3' end nucleotide sequences of an endogenous TARGETgene of interest, wherein the intervening oligonucleotide sequence between the 5' and 3' end nucleotide sequences comprises a prokaryotic, or non-mammalian, or unrelated mammalian DNA sequence and the overall size (number of base pair) of the STDgene is approximately identical to the amplicon size of the TARGETgene region of interest.

In accordance with an embodiment, the present invention provides one or more kits for determining the methylation status of a plurality of TARGETgene DNA sequences in a DNA sample. The invention kits include a plurality of copies of a STDgene specific for each TARGETgene of interest being detected, and one or more pairs of external methylation-independent PCR primers capable of selectively hybridizing to each of the one or more TARGETgenes being detected and capable of selectively hybridizing to each of the STDgenes under conditions that allow generation of a first amplification product containing first amplicons, and one or more pairs of internal methylation-dependent PCR primers specific for a gene of interest, one or more pairs of internal PCR primers specific for the SPS for each TARGETgene of interest, one or more optically detectable labeled DNA probes which specifically hybridize to a TARGETgene of interest, and one or more optically detectable labeled DNA probes which specifically hybridize to a STDgene for the gene of interest.

BRIEF DESCRIPTION OF THE DRAWINGS

FIG. 2 depicts a schematic diagram of an embodiment of the cMethDNA assay of the present invention. 2A) The first PCR reaction (STEP 1) is performed in multiplex to co-amplify 10 unique genes using one pair of primers per gene (forward and reverse). Each unique primer pair amplifies the gene of interest (TARGETgene) and 50 copies of matching cloned gene-specific standards (STDgene) spiked into the patient's serum before DNA purification. In the second PCR reaction (STEP 2), amplicons of each unique TARGETgene and STDgene gene set are assayed in the same well with gene specific sets of primers (forward and reverse) and hydrolysis probes (in two colors, recognizing TARGETgene or STDgene) using real-time PCR. 2B) Verification of array biomarker panel. The training set of 52 sera was tested by cMethDNA. 2C) Box plots of data in (2B) show that cancer sera display significantly higher median cumulative methylation than normal controls (p<0.0001).

DETAILED DESCRIPTION OF THE INVENTION

Figure 1:
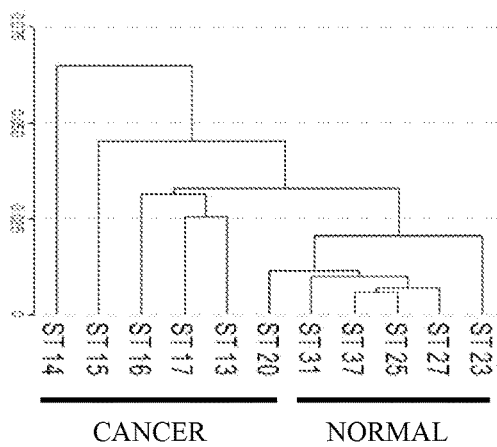
FIG. 1 depicts a genome-wide serum DNA methylation array in breast cancer. Serum samples obtained from individuals with breast cancer and normal controls were interrogated using the Infinium HumanMethylation27 BeadChip Array. 1A) Unsupervised two-dimensional hierarchical cluster analysis was performed on individual patient samples (X-axis) and probes (Y-axis) selected for good technical reproducibility within individual samples [probe detection p-value <0.00001; 26789/27578 array probes]. Two distinct clusters segregating according to cancer or normal sample origin are shown, indicating differences in genomic methylation profile(s) in the array. 1B) Scheme of criteria used for supervised selection of cancer-specific array probes. 1C) Average methylation level of each of 172 cancer specific probe (squares) is indicated in scatter plots for serum (left plot) and tissues (right plot) in sample groups of cancer (Y-axis) and normal (X-axis). The solid lines indicate region ±1.5-fold difference in average methylation level between groups (AVE_beta methylation) for individual CpG loci probes.
Figure 1:
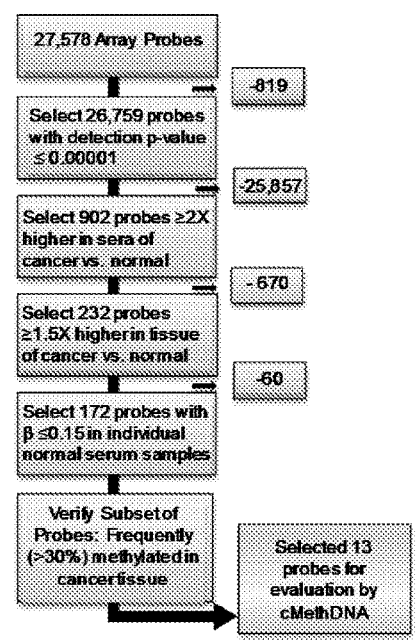
Figure 1:
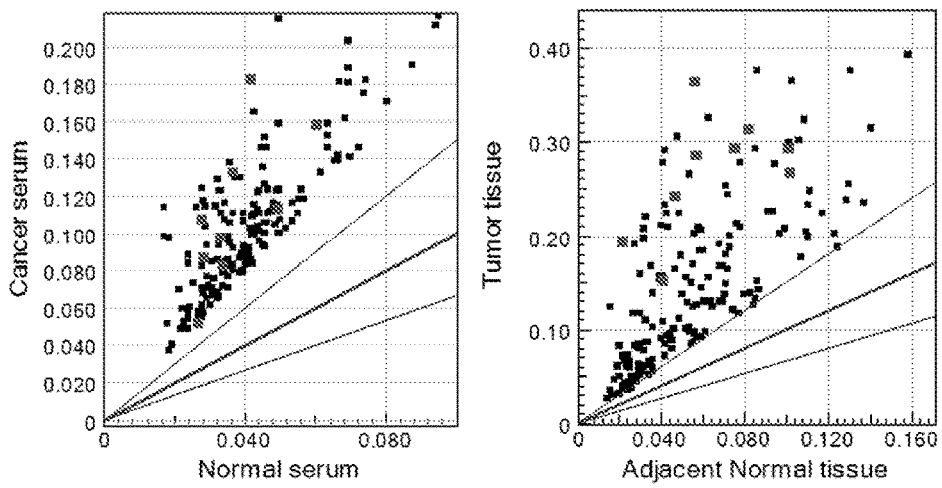

The inventive methods employ a modified two-step quantitative multiplex-methylation specific PCR (QM-MSP) approach, where many genes are co-amplified from amounts of sample previously used for just one gene and a combined methylation score can be generated for the panel of genes. The cMethDNA methods of the present invention combine the multiplex sensitivity QM-MSP with an increased quantitative signal to noise ratio due to the addition of the STDgene sequences, STDgene primers, and STDgene probes in the methods of the present invention. These novel cMethDNA methods allow a panel of a plurality of genes whose hypermethylation is associated with a disease or biological state, such as a type of carcinoma, for example, to be co-amplified from limiting amounts of DNA derived from samples sources of the subject being tested. cMethDNA overcomes known limitations of other serum MSP methods that cause lack of assay robustness, as described in the Background.

The inventive methods are also broadly applicable to evaluation of any of hundreds of genes from hypermethylated regions of genomic DNA derived from, but not limited to, human or non-human mammals, plants, and insects. For example, in mammals, such as humans, samples may be derived from bodily fluids, including, for example, one or more selected from blood, serum, plasma, ductal lavage fluid, nipple aspiration fluid, lymph, cerebrospinal fluid (CSF), and/or amniotic fluid from the subject being tested. In mammals, conditions associated with aberrant methylation of genes that can be detected or monitored include, but are not limited to, carcinomas and sarcomas of all kinds, including one or more specific types of cancer, e.g., breast cancer, an alimentary or gastrointestinal tract cancer such as colon, esophageal and pancreatic cancer, liver cancer, skin cancer, ovarian cancer, endometrial cancer, prostate cancer, lymphoma, hematopoietic tumors, such as leukemia, kidney cancer, lung cancer, bronchial cancer, muscle cancer, bone cancer, bladder cancer or brain cancer, such as astrocytoma, anaplastic astrocytoma, glioblastoma, medulloblastoma, and neuroblastoma, and their metastases. The inventive methods can be used to assay the DNA of any mammalian subject, including humans, pets (e.g., dogs, cats, ferrets), farm animals (meat and dairy), and race horses, for example.

Samples obtained from the fluid of other multicellular organisms, such as insects and plants, may also be evaluated for gene methylation status using the invention methods. For example, the methylation status of genes may serve as an indicator of heritability and flexibility of epigenetic states in such subjects. Thus, gene methylation is linked to acquisition of different characteristics in the organism.

The inventive methods combine the principles of quantitative multiplex methylation-specific PCR (QM-MSP) with addition of STDgene standards which are engineered specifically for the TARGETgene of interest. The studies described herein have shown that QM-MSP sensitivity is 1:100,000 and this combination of procedures (cMethDNA) can detect as few as 50 methylated copies of DNA. This outcome compares favorably to Q-MSP with a sensitively of 1:10,000 and conventional MSP with a sensitivity of 1:1000. In addition, reactions are specific since no cross-reactivity was observed between TARGETgene and STDgene primers even in mixtures consisting of more than $10^5$-fold excess of one or the other DNA.

Primer and Probe Design for cMethDNA. In practice of the inventive methods, the QM-MSP methodology was adapted to perform as cMethDNA by utilizing a single set of external primer pairs which hybridize to a single target gene of interest (TARGETgene) as well as to the respective STDgene for the TARGETgene in round one (pre-amplification) PCR in a manner independent of the methylation status of the TARGETgene, and in round two PCR (real time MSP) a methylation status-specific set of internal primers/probe hybridizing to the TARGETgene, as well as a TARGETgene standard-specific (i.e. STDgene) set of internal primers/probe hybridizing to the STDgene DNA. Thus each TARGETgene of interest has one pair of external primers and two sets of internal primer/probes, each internal set being designed specifically to detect and quantify the TARGETgene region of interest or the matched STDgene for each TARGETgene of interest (FIG. 2A).

A plurality of gene-specific external primer pairs may be used to co-amplify a plurality of TARGETgenes in what is termed multiplex PCR. Multiple external primer pairs used in the present inventive methods in one reaction can co-amplify a cocktail of TARGETgenes and their respective STDgenes, each pair selectively hybridizing to a member of the panel of TARGETgenes being investigated and their respective STDgenes using the inventive method. External primer pairs are designed to render DNA amplification independent of the methylation status of the DNA sequence. Therefore methylated TARGETgene and STDgene DNA sequences internal to the binding sites of the external primers are co-amplified for any given gene by a single set of external primers specific for that TARGETgene (and later quantified by real-time PCR using internal primers). For example, the sequences of the primers set forth in Table 1 below, and in the accompanying sequence listing, are used with the methods of the present invention are TARGETgenes associated with primary breast cancer.

TABLE 1

Primer Sequences for an Embodiment of the cMethDNA Assay

| Primer Name | 5' to 3' Sequence |
|---|---|
| AKR1B1_Ext_F | GYGTAATTAATTAGAAGGTTTTTT (SEQ ID NO: 1) |
| AKR1B1_Ext_R | AACACCTACCTTCCAAATAC (SEQ ID NO: 2) |
| AKR1B1_FM | GCGCGTTAATCGTAGGCGTTT (SEQ ID NO: 3) |
| AKR1B1_RM | CCCAATACGATACGACCTTAAC (SEQ ID NO: 4) |
| AKR1B1_M_Probe | CGTACCTTTAAATAACCCGTAAAATCGA (SEQ ID NO: 5) |
| AKR1B1_FUM | TGGTGTGTTAATTGTAGGTGTTTT (SEQ ID NO: 6) |
| AKR1B1_RUM | CCCAATACAATACAACCTTAACC (SEQ ID NO: 7) |
| AKR1B1_U_Probe | ACATACCTTTAAATAACCCATAAAATCAAC (SEQ ID NO: 8) |
| STD_AKR1B1_F | TTTGTTGATGTTTTGTGGAAGTAAG (SEQ ID NO: 9) |
| STD_AKR1B1_R | ATTCATCAATACTTTCAAATAACACA (SEQ ID NO: 10) |
| STD_AKR1B1_Probe | AAATACATTATCCTACCACTAACAATACA (SEQ ID NO: 11) |
| AKR1B1_Ext_F | GYGTAATTAATTAGAAGGTTTTTT (SEQ ID NO: 1) |

TABLE 1-continued

Primer Sequences for an Embodiment of the cMethDNA Assay

| Primer Name | 5' to 3' Sequence |
|---|---|
| STD_AKR1B1 Sequence | GYGTAATTAATTAGAAGGTTTTTTATTGGTTGTTAGGTA TTTGTATTGTTATTGTGATTGATGATTATTTTTTGATTG TTAGATAGTGGTGTTTTTGTTGATGTTTTGTGGAAGTAA GTGTATTGTTAGTGGTAGGATAATGTATTTGATGTGTTA TTTGAAAGTATTGATGAATGGTGTGGTGATTTATGATG G GTATTTGGAAGGTAGGTGTT (SEQ ID NO: 12) |
| ARHGEF7_F_Ext | YGTTTYGAGGTGAAGGYGYG (SEQ ID NO: 13) |
| ARHGEF7_R_Ext | CTCCAACAACCTACAAAAAC (SEQ ID NO: 14) |
| ARHGEF7_FM | GTTTTTCGGGTCGTAGCGATG (SEQ ID NO: 15) |
| ARHGEF7_RM | CAAAAAACCCTCCGAATCCGAA (SEQ ID NO: 16) |
| ARHGEF7_M_Probe | AAACCACGTAACGATTTACTCGACGA (SEQ ID NO: 17) |
| ARHGEF7_FUM2 | GTTGTAGTGATGAATTTTGTTGAG (SEQ ID NO: 18) |
| ARHGEF7_RUM2 | CAAAAAACCCTCCAAATCCAAAT (SEQ ID NO: 19) |
| ARHGEF7_U_Probe | AATAAACCACATAACAATTTACTCAACAAA (SEQ ID NO: 20) |
| STD_ARHGEF7_F | GGAAATGTGATTTTGATGTTTATGTT (SEQ ID NO: 21) |
| STD_ARHGEF7_R | ACCCAACACCTATTTCTTAATCAC (SEQ ID NO: 22) |
| STD_ARHGEF7_Probe | ACCTACACATCACTAACAAACATATACAA (SEQ ID NO: 23) |
| STD_ARHGEF7 Sequence | YGTTTYGAGGTGAAGGYGYGTGTTGATATGTTAGTGGG TTGGGGAAATGTGATTTTGATGTTTATGTTTATGTTTAT ATGGTATTTGGTAGATATTTTGTTGTATATGTTTGTTAG TGATGTGTAGGTTATGGTGATTAAGAAATAGGTGTTGG GTATTAGTGTGGTTTGGTTTTTTGTAGGTTGTTGGAG (SEQ ID NO: 24) |
| COL6A2_Ext_F | AGGTTTAGGAGAAGTTGTAGA (SEQ ID NO: 25) |
| COL6A2_Ext_R | TACCAACAATAAAAACCCAAAC (SEQ ID NO: 26) |
| COL6A2_FM | ATTCGGGTTGATAGCGATTCGT (SEQ ID NO: 27) |
| COL6A2_RM | CGATTCCACCAACGCCCCG (SEQ ID NO: 28) |
| COL6A2_M_Probe | ATCCCAAAACGAATATAAACGACCCG (SEQ ID NO: 29) |
| COL6A2_FUM | GATTTGGGTTGATAGTGATTTGTA (SEQ ID NO: 30) |
| COL6A2_RUM | CAATTCCACCAACACCCCAAC (SEQ ID NO: 31) |
| COL6A2_U_Probe | ATCCCAAAACAAATATAAACAACCCAAC (SEQ ID NO: 32) |
| STD_COL6A2_F | TTGGTAAGGTGGTGATGGTGAA (SEQ ID NO: 33) |
| STD_COL6A2_R | TCTTCTACCATCAACAAACATCC (SEQ ID NO: 34) |
| STD_COL6A2_Probe | AACTTTCACCATACAAATAATCACTTCC (SEQ ID NO: 35) |
| STD_COL6A2 Sequence | AGGTTTAGGAGAAGTTGTAGATGTTTTGTGGTTGGGTT AGTAGTATTGGTAAGGTGGTGATGGTGAAGGAAGTGAT TATTTGTATGGTGAAAGTTATTAATGTGGGATGTTTGTT GATGGTAGAAGATTGTAGTTTGGGTTTTTATTGTTGGTA (SEQ ID NO: 36) |
| GPX7_Ext_F | GGTGAAATTGAGGTTTAGAG (SEQ ID NO: 37) |
| GPX7_Ext_R | ATACTTCTCCAACRCACACCA (SEQ ID NO: 38) |
| GPX7_FM | ACGGTGGTAGCGGCGTGGTT (SEQ ID NO: 39) |
| GPX7_RM | ACCCCGAATATTAACCGCCTTA (SEQ ID NO: 40) |
| GPX7_M_Probe | TACTACGCGCAAACCGCAACCCAC (SEQ ID NO: 41) |

TABLE 1-continued

Primer Sequences for an Embodiment of the cMethDNA Assay

| Primer Name | 5' to 3' Sequence |
| --- | --- |
| GPX7_FUM | TGATGGTGGTAGTGGTGTGG (SEQ ID NO: 42) |
| GPX7_RUM | ACCCCAAATATTAACCACCTTAA (SEQ ID NO: 43) |
| GPX7_U_Probe | CTACTACACACAAACCACAACCCAC (SEQ ID NO: 44) |
| STD_GPX7_F | TGATAGTATTAGAAGGGATTGTAG (SEQ ID NO: 45) |
| STD_GPX7_R | CAAATCTAACCACATCCAAACTC (SEQ ID NO: 46) |
| STD_GPX7_Probe | AAATCACCTACCAATTCAACCATACCA (SEQ ID NO: 47) |
| STD_GPX7 Sequence | GGTGAAATTGAGGTTTAGAGGATGGAGGATGATGTAAT GTTGATGATAGTATTAGAAGGGATTGTAGGAGGAGTTT GGTATGGTTGAATTGGTAGGTGATTTGGTTGTTGATTTG AGTTTGGATGTGGTTAGATTTGATGAGTAGATGGTTAG AGTTAGGTGTTATTTTTTTGGTATGGAAAGTGATGTGAA AAAAATAGTGGTAGTTGTTGAATAGTTGTTGAGTTGAT AGGTGTTGGTTGTATAGAAAGTGGGGATTTTTGTTGGG TAGTATAAAGTGGTGTTGTTGGAGAAGTAT (SEQ ID NO: 48) |
| HIST1H3C_Ext_F2 | GTGTGTGTTTTTATTGTAAATGG (SEQ ID NO: 49) |
| HIST1H3C_Ext_R2 | ATAAAATTTCTTCACRCCACC (SEQ ID NO: 50) |
| HIST1H3C_FM2 | AATAGTTCGTAAGTTTATCGGCG (SEQ ID NO: 51) |
| HIST1H3C_RM2 | CTTCACGCCACCGATAACCGA (SEQ ID NO: 52) |
| HIST1H3C_M_Probe | TACTTACGCGAAACTTTACCGCCGA (SEQ ID NO: 53) |
| HIST1H3C_FUM2 | GTAAATAGTTTGTAAGTTTATTGGTG (SEQ ID NO: 54) |
| HIST1H3C_RUM2 | TTTCTTCACACCACCAATAACCAA (SEQ ID NO: 55) |
| HIST1H3C_U_Probe | AACTACTTACACAAAACTTTACCACCAA (SEQ ID NO: 56) |
| STD_HIST1H3C_F | GATTTAGAGTTGGATGTGTGGAT (SEQ ID NO: 57) |
| STD_HIST1H3C_R | ACCACCATACTAATAATCAAATCTA (SEQ ID NO: 58) |
| STD_HIST1H3C_Probe | AAATATCACTCATCACCAAATAAATCCAA (SEQ ID NO: 59) |
| STD_HIST1H3C Sequence | GTGTGTGTTTTTATTGTAAATGGTGGATTTAGAGTTGGA TGTGTGGATGGAGTTTTGGATTTATTTGGTGATGAGTGA TATTTTGGTATTGTTAGATTTGATTATTAGTATGGTGGT TA GGTGGTGTGAAGAAATTTTAT (SEQ ID NO: 60) |
| HOXB4_Ext_F | TTAGAGGYGAGAGAGTAGTT (SEQ ID NO: 61) |
| HOXB4_Ext_R | AAACTACTACTAACCRCCTC (SEQ ID NO: 62) |
| HOXB4_FM | CGGGATTTTGGGTTTTCGTCG (SEQ ID NO: 63) |
| HOXB4_RM | CGACGAATAACGACGCAAAAAC (SEQ ID NO: 64) |
| HOXB4_M_Probe | AACCGAACGATAACGAAAACGACGAA (SEQ ID NO: 65) |
| HOXB4_FUM3 | GTGGTGTGTATTGTGTAGTGTTA (SEQ ID NO: 66) |
| HOXB4_RUM2 | CAAACCAAACAATAACAAAAACAAC (SEQ ID NO: 67) |
| HOXB4_U2_Probe | CAAAATCCCAACAAACCACATAACACT (SEQ ID NO: 68) |
| STD_HOXB4_F | GTTAGTTTTGTAGTGTATTGAGTAT (SEQ ID NO: 69) |
| STD_HOXB4_R | CATCTTCCACAATAAACTTCCAATT (SEQ ID NO: 70) |
| STD_HOXB4_Probe | TAACTCCACCTATTCTACCTACCATTT (SEQ ID NO: 71) |
| STD_HOXB4 Sequence | TTAGAGGYGAGAGAGTAGTTTATATAATGGTGTGATTGT TATGTTTTTGAATTGTTAGTTTTGTAGTGTATTGAGTA TTTTGTTTTGATGAAATGGTAGGTAGAATAGGTGGAGT |

TABLE 1-continued

Primer Sequences for an Embodiment of the cMethDNA Assay

| Primer Name | 5' to 3' Sequence |
| --- | --- |
| | TAGATAGTAATTGGAAGTTTATTGTGGAAGATGTTATT<br>AGAATTGGTGTGTTTTGGTGGTGATGTTTTTGTGGTAT<br>AATTATTTGTAGAAGAGAGGTGGTTAGTAGTAGTTT<br>(SEQ ID NO: 72) |
| MAL_Ext_F | GATTTATAGTTTTTAGTTTTGGA (SEQ ID NO: 73) |
| MAL_Ext_R | AAACCACTAAACAAAATACTAC (SEQ ID NO: 74) |
| MAL_FM | TTTCGCGGAGTTAGCGAGAG (SEQ ID NO: 75) |
| MAL_RM | AAACCATAACGACGTACTAACG (SEQ ID NO: 76) |
| MAL_M_Probe | AAAACGAAACGAACGCCGCTCAAAC (SEQ ID NO: 77) |
| MAL_FUM | GTTTTGTGGAGTTAGTGAGAGG (SEQ ID NO: 78) |
| MAL_RUM | AAACCATAACAACATACTAACATC (SEQ ID NO: 79) |
| MAL_U_Probe | CTTAAAACAAAACAAACACCACTCAAAC (SEQ ID NO: 80) |
| STD_MAL_F | GTGTGGGATGTGTTTAGTGATTT (SEQ ID NO: 81) |
| STD_MAL_R | CAATCCTACACAAACATCAACAT (SEQ ID NO: 82) |
| STD_MAL_Probe | GGTGATGTGTTGTATGTTGGTATGG (SEQ ID NO: 83) |
| STD_MAL Sequence | GATTTATAGTTTTTAGTTTTGGATGTGGTGGATGTGGAT<br>AAATGGGTGTTGTATGTTATTGGTTAGTATTGTGATTAG<br>TTAGTGTTGGATGGTTTTGGTGGTATGGAGTTGTGTATT<br>ATTTGTAATGTGTATTTGATTATATAGTGTAAGGTGTGG<br>GATGTGTTTAGTGATTTTTGTTTGGTGATGTGTTGTATG<br>TTGGTATGGAATGGGTAGATGTTGATGTTTGTGTAGGA<br>TTGATTGTTGGATAAGATGTGGATTTATAATTGTAGTAA<br>TGTGGTGATGTTGGATGATGGTGGTAGTATTTTGTTTAG<br>TGGTTT (SEQ ID NO: 84) |
| RASGRF2_Ext_F | GAGGGAGTTAGTTGGGTTAT (SEQ ID NO: 85) |
| RASGRF2_Ext_R | CCTCCAAAAAATACATACCC (SEQ ID NO: 86) |
| RASGRF2_FM | GTAAGAAGACGGTCGAGGCG (SEQ ID NO: 87) |
| RASGRF2_RM | ACAACTCTACTCGCCCTCGAA (SEQ ID NO: 88) |
| RASGRF2_M_Probe | AACGAACCACTTCTCGTACCAACGA (SEQ ID NO: 89) |
| RASGRF2_FUM | GAGTAAGAAGATGGTTGAGGTG (SEQ ID NO: 90) |
| RASGRF2_RUM | CAACAACTCTACTCACCCTCAA (SEQ ID NO: 91) |
| RASGRF2_U_Probe | AAACAAACCACTTCTCATACCAACAAC (SEQ ID NO: 92) |
| STD_RASGRF2_F | TGTATGAGTTTGTGGTGAATAATG (SEQ ID NO: 93) |
| STD_RASGRF2_R | AACTCACCATCAAACACTTTCCC (SEQ ID NO: 94) |
| STD_RASGRF2_Probe | TACAAACCCAACATCCTCTATCTATTC (SEQ ID NO: 95) |
| STD_RASGRF2 Sequence | GAGGGAGTTAGTTGGGTTATTAGGAAGTGTTTATTATTT<br>GGTTTATGGAGGTAATTTTTTATGTTGAAAATGTGGTGT<br>ATTGGTTGTTTGGTATGTATGAGTTTGTGGTGAATAATG<br>TTTTTGAATAGATAGAGGATGTTGGGTTTGTAGAGTTTG<br>TTTTTGTGGGAAAGTGTTTGATGGTGAGTTGAGTTTTGT<br>TTTGAAATTGGTGTGTGAGATGGGGTGATTTGATTGGT<br>GTGTTATGTTTGTTGGGATGTTATTTATGGAGGGTATGT<br>ATTTTTTTGGAGG (SEQ ID NO: 96) |
| RASSF1A_Ext_F2 | GTTTTATAGTTTTTGTATTTAGG (SEQ ID NO: 97) |
| RASSF1A_Ext_R2 | AACTCAATAAACTCAAACTCCC (SEQ ID NO: 98) |
| RASSF1A_FM | GCGTTGAAGTCGGGGTTC (SEQ ID NO: 99) |
| RASSF1A_RM | CCCGTACTTCGCTAACTTTAAACG (SEQ ID NO: 100) |

TABLE 1-continued

Primer Sequences for an Embodiment of the cMethDNA Assay

| Primer Name | 5' to 3' Sequence |
|---|---|
| RASSF1A_M-Probe | ACAAACGCGAACCGAACGAAACCA (SEQ ID NO: 101) |
| RASSF1A_RT-FUM | GGTGTTGAAGTTGGGGTTTG (SEQ ID NO: 102) |
| RASSF1A_RT-RUM | CCCATACTTCACTAACTTTAAAC (SEQ ID NO: 103) |
| RASSF1A_U_Probe | CTAACAAACACAAACCAAACAAAACCA (SEQ ID NO: 104) |
| STD_RASSF1A_F2 | TTAGGGTAGATTGTGGATATTAG (SEQ ID NO: 105) |
| STD_RASSF1A_R3 | ATACTAACAACTATCCAATACAAC (SEQ ID NO: 106) |
| STD_RASSF1A_Probe 2 | AGGTTGAAATTAGTATGTGTTATTTTGGTATGG (SEQ ID NO: 107) |
| STD_RASSF1A Sequence | TAGAATTCGTTTTATAGTTTTTGTATTTAGGGTAGATTG TGGATATTAGATAGGTTGAAATTAGTATGTGTTATTTTG GTATGGTGTTGTATTGGATAGTTGTTAGTATTAATATTA AATTGGGTTATGATTATTATTTTTATATTTGTAGTGTGA ATATTGTTGGTAAATTGGTATTTGTGGAGGGAGTTTGA GTTTATTGAGTT (SEQ ID NO: 108) |
| TM6SF1_Ext_F | AGGAGATATYGTTGAGGGGA (SEQ ID NO: 109) |
| TM6SF1_Ext_R | TCACTCATACTAAACCRCCAA (SEQ ID NO: 110) |
| TM6SF1_FM | CGTTTAGCGGGATGCGGTGA (SEQ ID NO: 111) |
| TM6SF1_RM | ACACGAAAACCCCGATAACCG (SEQ ID NO: 112) |
| TM6SF1_M_Probe | AAACACTCATCGCAACCGCCGCG (SEQ ID NO: 113) |
| TM6SF1_FUM | TGTTTAGTGGGATGTGGTGAAG (SEQ ID NO: 114) |
| TM6SF1_RUM | ACACAAAAACCCCAATAACCACA (SEQ ID NO: 115) |
| TM6SF1_U_Probe | AAACACTCATCACAACCACCACACC (SEQ ID NO: 116) |
| STD_TM6SF1_F | TTAGATGTTGATTGGTTGTGTTTG (SEQ ID NO: 117) |
| STD_TM6SF1_R | ATCATCATAAAACTCAACAATCAATT (SEQ ID NO: 118) |
| STD_TM6SF1_Probe | CCAAACATCAAATCTTTAACTTTTACCAA (SEQ ID NO: 119) |
| STD_TM6SF1 Sequence | AGGAGATATYGTTGAGGGGAGAGGATGTTATGTTTGTA TTAAATTTTATAATGTTGGTGAAAGGTGTTGGGATTATT TTGTGGGTTTATAAGGGGAGTGGTGATTTTTATGTGAAT TTGTTTTTAGATGTTGATTGGTTGTGTTTGGTAAAAGTT AAAGATTTGATGTTTGGTGAATTGATTGTTGAGTTTTAT GATGATAGTTATTTTGATGATGAAGATGTAGATTGGAT TTGGTGGTTTAGTATGAGTGA (SEQ ID NO: 120) |
| TMEFF2_Ext F | TTATGGTAGTAGTTTTTYGYGTT (SEQ ID NO: 121) |
| TMEFF2_Ext R | CCCACAACACCATAACTAATTC (SEQ ID NO: 122) |
| TMEFF2_FM | TTTCGTTTCGGGGTTGAGTTTAG (SEQ ID NO: 123) |
| TMEFF2_RM | ACGATAACAATAACACCCGACGA (SEQ ID NO: 124) |
| TMEFF2_M_Probe | CAAACCCGCGCATAATCTCGAAAATT (SEQ ID NO: 125) |
| TMEFF2_FUM | TTTTGTTTTGGGGTTGAGTTTAGTT (SEQ ID NO: 126) |
| TMEFF2_RUM | CAACAATAACAATAACACCCAACAA (SEQ ID NO: 127) |
| TMEFF2_U_Probe | CAAACCCACACATAATCTCAAAATTTC (SEQ ID NO: 128) |
| STD_TMEFF2_F | ATTAGTGAAGGGTTGATTGAAGG (SEQ ID NO: 129) |
| STD_TMEFF2_R | CCAAATATATTAATATTCCCCTCAA (SEQ ID NO: 130) |
| STD_TMEFF2_Probe | ACCAACATACTATTCAACAACACACTTT (SEQ ID NO: 131) |
| STD_TMEFF2 Sequence | TTATGGTAGTAGTTTTTYGYGTTATGGGTAAAGGAAGT AGTAAGGGGTATATTTTGTGTGAAGTGAAGGATAATTT GAAGTTTATGTAGTTGTTGAGTGTGATTGATGTTATTAG |

TABLE 1-continued

Primer Sequences for an Embodiment of the cMethDNA Assay

| Primer Name | 5' to 3' Sequence |
| --- | --- |
| | TGAAGGGTTGATTGAAGGTTTGGTGGATGGTTTAAAAA GTGTGTTGTTGAATAGTATGTTGGTGTTGGATATTGAGG GGAATATTAATATATTTGGTGTTATGGTGGTGTTTTGGG TTGGTGAGTAGGAGTAGATTTTGGAATTAGTTATGGTG TTGTGGG (SEQ ID NO: 132) |
| TWIST_Ext_F3 | GAGATGAGATATTATTTATTGTG (SEQ ID NO: 133) |
| TWIST_Ext_R4 | CCTCCCAAACCATTCAAAAAC (SEQ ID NO: 134) |
| TWIST_FM | GTTAGGGTTCGGGGGCGTTGTT (SEQ ID NO: 135) |
| TWIST_RM | CCGTCGCCTTCCTCCGACGAA (SEQ ID NO: 136) |
| TWIST_M_Probe | AAACGATTTCCTTCCCCGCCGAAA (SEQ ID NO: 137) |
| TWIST_FUM3a | TTAGGGTTTGG GGGTGTTGTTTGTATG (SEQ ID NO: 138) |
| TWIST_RUM5 | CCATCACCTTCCTCCAACAAAC (SEQ ID NO: 139) |
| TWIST_U_Probe | AAACAATTTCCTTCCCCACCAAAACA (SEQ ID NO: 140) |
| STD_TWIST_F | TTGTATTTATTGATTTGGTAAATGGG (SEQ ID NO: 141) |
| STD_TWIST_R | ACATCATTCATAAATATCTAATTACC (SEQ ID NO: 142) |
| STD_TWIST_Probe | ACACCACAAACATCAACATTTCATTCCC (SEQ ID NO: 143) |
| STD_TWIST Sequence | GAGATGAGATATTATTTATTGTGATATGGAGGAAGGTA AATTGAGTTAGTTTTTGGTTGTTGTTAATTGTATTGTAT TTATTGATTTGGTAAATGGGAATGAAATGTTGATGTTTG TGGTGTAGGGTAATTAGATATTTATGAATGATGTGTTTT TGAAGTGTTTGATGGTTTTTATTATTATTAGTGGTGGTA ATTTTTTGGTTTTTTTTTGATATTGGATGGAAAGTTGAT TGTTAAAAATGTGGATATTGTTTTTGAATGGTTTGGGAG G (SEQ ID NO: 144) |
| ALX1_Ext_F | AGTAAAGYGTTTGTAGGTAAAT (SEQ ID NO: 145) |
| ALX1_Ext_R | TTTCTCCCTCCCTACCTAAT (SEQ ID NO: 146) |
| ALX1_FM | CGTGCGTTTGGAGAGGATTTC (SEQ ID NO: 147) |
| ALX1_RM | CGATCCTACATTTTCGATTACGA (SEQ ID NO: 148) |
| ALX1_M_Probe | AACGCTAACGACTCACCGCTACTAT (SEQ ID NO: 149) |
| ALX1_FUM | ATGTGTGTTTGGAGAGGATTTTG (SEQ ID NO: 150) |
| ALX1_RUM | ACCAATCCTACATTTTCAATTACAA (SEQ ID NO: 151) |
| ALX1_U_Probe | TAAAACACTAACAACTCACCACTACTAT (SEQ ID NO: 152) |
| STD_ALX1_F | GAGGGTGTAATTGATAAGAGTTTT (SEQ ID NO: 153) |
| STD_ALX1_R | CCTACAACAACACCATTCACAAT (SEQ ID NO: 154) |
| STD_ALX1_Probe | ATCATACCACTAACCAACACAATAACTT (SEQ ID NO: 155) |
| STD_ALX1 Sequence | AGTAAAGYGTTTGTAGGTAAATAGGGTAGAGTATTATG TTGATTGTGGTTTTTTAGTTGGAGGGTGTAATTGATAAG AGTTTTTGTGTGGTGTTTGTGGATAAAATAAAAGTTATT GTGTTGGTTAGTGGTATGATTATTATTGTGAATGGTGTT GTTGTAGGTAAGGTTAATTAGGTAGGGAGGGAGAAA (SEQ ID NO: 156) |
| DAB1_Ext_F | GGATTTGTTAGTTTTAGGGAA (SEQ ID NO: 157) |
| DAB1_Ext_R | ACACAATATTACAAACCACCA (SEQ ID NO: 158) |
| DAB1_FM | AAAGCGGAGTTCGTTCGTTTTTT (SEQ ID NO: 159) |
| DAB1_RM | CTACCTCCAACCGCCGAAAAC (SEQ ID NO: 160) |
| DAB1_M_Probe | ACCCTCTCGACTCATCCTCCGAC (SEQ ID NO: 161) |

TABLE 1-continued

Primer Sequences for an Embodiment of the cMethDNA Assay

| Primer Name | 5' to 3' Sequence |
| --- | --- |
| DAB1_FUM | AAAGTGGAGTTTGTTTGTTTTTTATT (SEQ ID NO: 162) |
| DAB1_RUM | CTACCTCCAACCACCAAAAACC (SEQ ID NO: 163) |
| DAB1_U_Probe | AACCCTCTCAACTCATCCTCCAACT (SEQ ID NO: 164) |
| STD_DAB1_F | TGGGTTGATGTATATTGTGTTTAG (SEQ ID NO: 165) |
| STD_DAB1_R | AACCTCACACCAATTCAACAAAC (SEQ ID NO: 166) |
| STD_DAB1_Probe | AAATCCAACAAATACATATCCAAATCACT (SEQ ID NO: 167) |
| STD_DAB1 Sequence | GGATTTGTTAGTTTTAGGGAATGGGTTGATGTATATTGT GTTTAGTTTGTTTTTTAGTGATTTGGATATGTATTTGTTG GATTTTAGTTTGTTGAATTGGTGTGAGGTTGATGAAGA GTTTGAAGATGATGTGTTGATGTAGAAAGTGGTAGGGT TTGTTGGAGGTGTTTGTTTTGGTTTGGATGGGAATGAAG TTATTTTTGTTTTTTTGGATGTGGTGGATATTGGTGGTTT GTAATATTGTGT (SEQ ID NO: 168) |
| DAB2IP_EXT_F3 | TTTAGGGGTTTTTAAGGTAGG (SEQ ID NO: 169) |
| DAB2IP_EXT_R3 | AAAAACCCTATACCTCCCTC (SEQ ID NO: 170) |
| DAB2IP_FM_3 | GGTATCGTACGGTTCGGGAAA (SEQ ID NO: 171) |
| DAB2IP_RM_3 | AACGAAACCGAACGCGAAATCC (SEQ ID NO: 172) |
| DAB2IP_M3_Probe | ATCCTACCTCGCCTATCCGAAATAAACA (SEQ ID NO: 173) |
| DAB2IP_FUM3 | TTGGGTATTGTATGGTTTGGGAA (SEQ ID NO: 174) |
| DAB2IP_RUM3 | AAACAAAACCAAACACAAAATCCC (SEQ ID NO: 175) |
| DAB2IP_U3_Probe | TCCTACCTCACCTATCCAAAATAAACA (SEQ ID NO: 176) |
| STD_DAB2IP_F | TTGTTAGTGGTGTAGTATTTGATTG (SEQ ID NO: 177) |
| STD_DAB2IP_R | ACCTTCAATATATCCCATCACAC (SEQ ID NO: 178) |
| STD_DAB2IP_Probe | AATATTCCCCACTATCTACAATAACTTC (SEQ ID NO: 179) |
| STD_DAB2IP Sequence | TTTAGGGGTTTTTAAGGTAGGAGAGTGGTATGGTGAAT GGTGTTATGTTGTTAGTGGTGTAGTATTTGATTGTAGAA GTTATTGTAGATAGTGGGGAATATTAGGTGTTGGTGTG ATGGGATATATTGAAGGTGGTGAAGGGTGTGAGTTTTT TGTTTTGTTTGATTGTAATAGTGGATGATGGTAGTGAGT GGTTGGTTAGTGAGGGAGGTATAGGGTTTTT (SEQ ID NO: 180) |
| GAS7C_Ext_F | GTAAGGGTTGTTTTTYGGGG (SEQ ID NO: 181) |
| GAS7C_Ext_R | AACCCTATACCCCTTCTCC (SEQ ID NO: 182) |
| GAS7C_FM | TAGGTACGCGAGCGTATCGAG (SEQ ID NO: 183) |
| GAS7C_RM | CCGACGAACTACGTACAATTAC (SEQ ID NO: 184) |
| GAS7C_M_Probe | TCGTAGTTTCGGTTTTTATAGTTTCGGT (SEQ ID NO: 185) |
| GAS7C_FUM | TAATAGGTATGTGAGTGTATTGAG (SEQ ID NO: 186) |
| GAS7C_RUM | TTCCCAACAAACTACATACAATTAC (SEQ ID NO: 187) |
| GAS7C_U_Probe | TTGTAGTTTTGGTTTTTATAGTTTTGGT (SEQ ID NO: 188) |
| STD_GAS7C_F | ATGTAGATTGTGGATTTTAGTGTTG (SEQ ID NO: 189) |
| STD_GAS7C_R | ATACCAACATAATCATCATCACAAAT (SEQ ID NO: 190) |
| STD_GAS7C_Probe | TTTTGTTATGTATTGGGTGATGTTATTGA (SEQ ID NO: 191) |
| STD_GAS7C Sequence | GTAAGGGTTGTTTTTYGGGGTGTGGTTGATTAAAATAG AATTGTTGGAAATGTAGATTGTGGATTTTAGTGTTGGTG TAGAAGGGTTTTGTTATGTATTGGGTGATGTTATTGAAA TTTGTGATGATGATTATGTTGGTATTAGTATTGGTGGTT GTGTGTTGGTGGCGAATAGTTAGATTTGGATGTTGATG |

TABLE 1-continued

Primer Sequences for an Embodiment of the cMethDNA Assay

| Primer Name | 5' to 3' Sequence |
|---|---|
| | TTTGATTGTGAAATTATGTTGTTATTTTTGGTATTGTGT
TGATAAGTTTGGTTGATGGAAGTGGTAATTTGGTTAGT
GGAGAAGGGGTATAGGGTT (SEQ ID NO: 192) |
| GSTP1_Ext_F | TGGGAAAGAGGGAAAGGTTT (SEQ ID NO: 193) |
| GSTP1_Ext_R | TACTCACTAATAACRAAAACTAC (SEQ ID NO: 194) |
| GSTP1_FM2 | CGGTCGGCGTCGTGATTTAG (SEQ ID NO: 195) |
| GSTP1_RM2 | AACTCCAACGAAAACCTCGCG (SEQ ID NO: 196) |
| GSTP1_M2_probe | AAAATAATCCCGCCCCGCTCCGC (SEQ ID NO: 197) |
| GSTP1_FUM2 | GTGGTTGGTGTTGTGATTTAGTA (SEQ ID NO: 198) |
| GSTP1_RUM2 | AACTCCAACAAAAACCTCACAAC (SEQ ID NO: 199) |
| GSTP1_U_Probe | AAAAATAATCCCACCCCACTCCACC (SEQ ID NO: 200) |
| STD_GSTP1_F | GGTGTTGTTGATTATGGTGTTTAA (SEQ ID NO: 201) |
| STD_GSTP1_R | TACTACAACACATAACCCAACTC (SEQ ID NO: 202) |
| STD_GSTP1_Probe | AACATTCACACCATATCCACTCAATATT (SEQ ID NO: 203) |
| STD_GSTP1 Sequence | TGGGAAAGAGGGAAAGGTTTGTGGTATGTTATGTAGTG
TGTGGTTGGGAAAAATTGTTATTTTATTGATGTGGTGAA
AATTTTGATGGTGGTGTTGTTGATTATGGTGTTTAAATA
AAATATTGAGTGGATATGGTGTGAATGTTTTTTGAAAG
AGTTGGGTTATGTGTTGTAGTATTAATTGAGGATGGTA
ATAAAGTGATGAAATATATTGAATTTTGTGTAGTTGTAT
TGGGTAGTTTTTGTTATTAGTGAGTA (SEQ ID NO: 204) |
| HIN1_Ext_R3 | AAACTACAAAACAAAACCAC (SEQ ID NO: 205) |
| HIN1_Ext_F2 | GTTTGTTAAGAGGAAGTTTT (SEQ ID NO: 206) |
| HIN1_FM | TAGGGAAGGGGGTACGGGTTT (SEQ ID NO: 207) |
| HIN1_RM | CGCTCACGACCGTACCCTAA (SEQ ID NO: 208) |
| HIN1_M_probe | ACTTCCTACTACGACCGACGAACC (SEQ ID NO: 209) |
| HIN1_FUM2 | AAGTTTTTGAGGT TTGGGTAGGGA (SEQ ID NO: 210) |
| HIN1_RUM2 | ACCAACCTCACCCACACTCCTA (SEQ ID NO: 211) |
| HIN1_U_Probe | CAACTTCCTACTACAACCAACAAACC (SEQ ID NO: 212) |
| STD_HIN1_F | ATAATGTTAGTAGATTGGAGGAGTT (SEQ ID NO: 213) |
| STD_HIN1_R | AACCCACATAACATTCCACTTATC (SEQ ID NO: 214) |
| STD_HIN1_Probe | AAAGAGTGGGAGGATGTTAGTGATAAGTG (SEQ ID NO: 215) |
| STD_HIN1 Sequence | GTTTGTTAAGAGGAAGTTTTGTGAGTGATGATGTGGAA
GGTTATTTGGATTTTTTTAAAGGTAAGATAATTGAATTT
TATTTTGGTAAGGAGTTGTTGGAAAAAGTTGAGTTGAT
GGAGGATAATGTTAGTAGATTGGAGGAGTTTTTGAAAG
AGTGGGAGGATGTTAGTGATAAGTGGAATGTTATGTGG
GTTGTTAAAATTGAGTAGATTAAAGATGGTAAATATTA
TGTTGTGGGTATTGTGGTTTTGTTTTGTAGTTT (SEQ ID NO: 216) |
| HIC1_Ext_F | TTTAGTTGAGGGAAG GGGAA (SEQ ID NO: 217) |
| HIC1_Ext_R | AACTACAACAACAACTACCTAA (SEQ ID NO: 218) |
| HIC1_FM | GGTTAGGCGGTTAGGGCGTC (SEQ ID NO: 219) |
| HIC1_RM | CCGAACGCCTCCATCGTATC (SEQ ID NO: 220) |
| HIC1_M_Probe | CACACACCGACCGAATAAAAACCGT (SEQ ID NO: 221) |
| HIC1_FUM | GGGTTAGGTGGTTAGGGTGTT (SEQ ID NO: 222) |

TABLE 1-continued

Primer Sequences for an Embodiment of the cMethDNA Assay

| Primer Name | 5' to 3' Sequence |
| --- | --- |
| HIC1_RUM | TAACCAAACACCTCCATCATATC (SEQ ID NO: 223) |
| HIC1_U_Probe | AAACACACACCAACCAAATAAAAACCAT (SEQ ID NO: 224) |
| STD_HIC1_F | GGAATTGGATTGATTTGAATAATGG (SEQ ID NO: 225) |
| STD_HIC1_R | AAAACATCCATCTTCATAACATTAC (SEQ ID NO: 226) |
| STD_HIC1_Probe | ATAACAAACAATAACCTACATATCTTCAAC (SEQ ID NO: 227) |
| STD_HIC1 Sequence | TTTAGTTGAGGGAAGGGGAATTGGATTGATTTGAATAATGGTTGGGAGATGGTGATAGAGTTTGTTGAAGATATGTAGGTTATTGTTTGTTATGGTTGTAATGTTATGAAGATGGATGTTTTGGTTGTATTAGTTGGGGGTAGGTATATTTTAGGTAGTTGTTGTTGTAGTT (SEQ ID NO: 228) |
| RARB2_Ext_F3 | GTATAGAGGAATTTAAAGTGTG (SEQ ID NO: 229) |
| RARB2_Ext_R3 | TCTTTCCTATTTCTCACCTTAA (SEQ ID NO: 230) |
| RARB2_FM3 | GGCGTAGGCGGAATATCGTTT (SEQ ID NO: 231) |
| RARB2_RM3 | AAACCGAAACGCTACTCCTAAC (SEQ ID NO: 232) |
| RARB2_M3_Probe | ACGCCTTTTTATTTACGACGACTTAAC (SEQ ID NO: 233) |
| RARB2_FUM3 | TGGGTGTAGGTGGAATATTGTTT (SEQ ID NO: 234) |
| RARB2_RUM3 | AACCAAAACACTACTCCTAACTC (SEQ ID NO: 235) |
| RARB2_UM3_Probe | TTTACACCTTTTTATTTACAACAACTTAAC (SEQ ID NO: 236) |
| STD_RARB2_F | GTTGTAATGGTTATTAATTGTGTTG (SEQ ID NO: 237) |
| STD_RARB2_R | CCCTTTCCTTTACCAATTTCCA (SEQ ID NO: 238) |
| STD_RARB2_Probe | ATCTCACAAACAACCTATAACACCAAC (SEQ ID NO: 239) |
| STD_RARB2 sequence | GTATAGAGGAATTTAAAGTGTGATTAGTAAAATGGTGGTGTTTGGTGTTGTTGTAATGGTTATTAATTGTGTTGTTTTATTTGTGATATTGTAGTTGGTGTTATAGGTTGTTTGTGAGATAAAGGTATGTTGGAAATTGGTAAAGGAAAGGGTTAGGTTGAAAAGGGTTATGGTTAAAAATTTGTAGGTTAGAATTAAAGTTAAGGTGAGAAATAGGAAAGA (SEQ ID NO: 240) |

Internal PCR primers used for quantitative real-time PCR of methylated TARGETgene DNA sequences of interest and for the respective STDgene for the targeted endogenous gene(s) of interest (round two cMethDNA) are designed to selectively hybridize to the amplicon(s) produced by the first round of PCR for one or more members of the panel of TARGETgene DNA sequences being investigated, using the inventive methods to detect the methylation status, i.e., whether methylated (M) CpG residues are present within the amplified region of the CpG island(s). Thus for each member of the starting panel of DNA sequences used in an invention assay, separate round two cMethDNA reactions are conducted to amplify the amplicons produced in the first round of PCR using the respective methylation-specific internal primer pair and using the respective STDgene-specific internal primer pair. Round two of the cMethDNA methodology quantifies amplicons from regions of the TARGETgene and STDgene synthesized in round one. During round two real-time PCR the TARGETgene and respective STDgene can be assayed separately in individual wells or together in one well if both internal primer/probe sets are present in the same well and two differentiable detectable labels, such as distinctly different fluorescent labels and quenchers are used for the respective probes (e.g. 6FAM/TAMRA and VIC/TAMRA).

It will be understood by those of skill in the art, that the methods of the present invention can be used to quantify methylated and unmethylated DNA. However, it is important to note that for various reasons, the quantity of unmethylated DNA in patients can fluctuate daily, and as such, it is less than optimal to compare methylated DNA quantity to a fluctuating reference point.

As used herein, the term "STDgene" means an oligonucleotide which is recombinantly inserted into a carrier DNA sequence to match the targeted endogenous gene (TARGETgene) of interest. Nucleotides at the 5' and 3' ends of the STDgene (approximately 20-22 bp hybridizing to forward and reverse external primers) are the same in sequence as the endogenous genomic DNA of interest (TARGETgene); and the number of intervening bases between the 5' and 3' regions in the STDgene oligonucleotide is essentially the same as the region of interest within the TARGETgene. To prevent cross-hybridization with human DNA, in an embodiment, the intervening bases between 5' and 3' ends consist of lambda phage DNA in the standard. To prevent cross-hybridization between standards (e.g. during the first round multiplex reaction), in an embodiment, each STDgene type has a unique lambda phage DNA sequence. In accordance with one or more alternate embodiments, the intervening bases comprise any irrelevant DNA lacking homology to the region of the gene(s) of interest. This combination of features allows for co-amplification of the TARGETgene and STDgene in the multiplex reaction using a single set of external forward and reverse primers and later quantitation of these amplicons using specific primer/probes by real-time PCR in round two.

In round one multiplex PCR; there is a direct relationship between the number of copies of TARGETgene and STDgene DNAs amplified because each external forward and reverse primer has an equal chance of hybridizing to the target as it has to the STDgene (cloned to have 5' and 3' ends identical to the TARGETgene), providing the TARGETgene is present. Thus, for each TARGETgene the cMethDNA set includes: 1) external primers, forward and reverse, 2) TARGETgene methylation status-specific internal primers, forward and reverse, 3) STDgene-specific internal primers, forward and reverse, 4) probes to match #2 and #3, individually in distinct colors (e.g., 6FAM/TAMRA or VIC/TAMRA, or other combinations).

In round two of cMethDNA, when a single gene or standard is amplified, the event is detected with a distinguishable fluorescence labeled probe, and the intensity of signal doubles with each round of PCR (at 100% efficiency). The probes used in round two cMethDNA of the inventive methods are designed to selectively hybridize to the segment of the amplicon lying between the binding sites of the respective internal PCR primer pair. Polynucleotide probes suitable for use in real-time PCR include, but are not limited to, a bilabeled oligonucleotide probe, such as a molecular beacon or a TaqMan™ probe, which include a fluorescent moiety and a quencher moiety. In a molecular beacon the fluorescence is generated due to hybridization of the probe, which displaces the quencher moiety from proximity of the fluorescent moiety due to disruption of a stem-loop structure of the bilabeled oligonucleotide. Molecular beacons, such as Amplifluor™ or TriStar™ reagents and methods are commercially available (Stratagene; Intergen). In a TaqMan™ probe, the fluorescence is progressively generated due to progressive degradation of the probes by Taq DNA polymerase during rounds of amplification, which displaces the quencher moiety from the fluorescent moiety. Once amplification occurs, the probe is degraded by the 5'-3' exonuclease activity of the Taq DNA polymerase, and the fluorescence can be detected, for example by means of a laser integrated in the sequence detector. The fluorescence intensity, therefore, is proportional to the amount of amplification product produced. Examples of fluorescent dyes which can be used with the inventive methods include 6-FAM, JOE, TET, Cal FLUOR Gold, Cal FLUOR Orange, Cal FLUOR Red, HEX, TAMRA, Cy3, Cy5, Cy5.5, Quasar 570, Quasar 670, ROX, and Texas Red. Examples of quenchers which can be used with the inventive methods include BHQ-1, BHQ-2, BHQ-3, and TAMRA.

In an embodiment, fluorescence from the probes are detected and measured during a linear amplification reaction and, therefore, can be used to detect the copy number of the amplification product.

In some embodiments, amplicons in the 75-150 base pair range are generally favored for the internal PCR assay because they promote high-efficiency assays which enable absolute quantitation to be performed. Quantitation of the copy number of STDgene and methylated TARGETgene amplicons for a specific gene is an improvement over the need to use as a reference unmethylated (U) DNA of the same gene or actin to estimate of DNA input, as described in the Background. Each respective STDgene has been designed with similar structural features (same amplicon length, and homologous bases at the 5' and 3' ends) as the region of interest in the specific TARGETgene (derived from round one, multiplex PCR of cMethDNA).

Whenever possible, primers and probes for the target gene region of interest can be selected in a region with a G/C content of 20-80%. Regions with G/C content in excess of this may not denature well during thermal cycling, leading to a less efficient reaction. In addition, G/C-rich sequences are susceptible to non-specific interactions that may reduce reaction efficiency. For this reason, primer and probe sequences containing runs of four or more G bases are generally avoided. A/T-rich sequences require longer primer and probe sequences in order to obtain the recommended melting temperatures (TMs). This is rarely a problem for quantitative assays; however, TaqMan™ probes approaching 40 base pairs can exhibit less efficient quenching and produce lower synthesis yields.

Examples of external primer pairs, internal primer pairs and gene-specific probes and respective STDgene for determining the methylation status of TARGETgenes associated with primary breast cancer are set forth in Table 1.

Examples of genes of interest (TARGETgene) used in the inventive methods include, but are not limited to, AKR1B1, ARHGEF7, COL6A2, GPX7, HIST1H3C, HOXB4, MAL, RASGRF2, RASSF1A, TM6SF1, TMEFF2, TWIST1, ALX1, DAB1, DAB2IP, GAS7C, GSTP1, HIN1, HIC1, and RARB2.

The TaqMan™ probe used in the Example herein contains both a fluorescent reporter dye at the 5' end, such as 6-carboxyfluorescein (6-FAM: emission $\lambda_{max}$=518 nm) and a quencher dye at the 3' end, such as 6-carboxytetramethylrhodamine, (TAMRA; emission $\lambda_{max}$=582 nm). The quencher can quench the reporter fluorescence when the two dyes are close to each other, which happens in an intact probe. Other reporter dyes include but are not limited to VIC™ and TET™ and these can be used in conjunction with 6-FAM to co-amplify genes by quantitative real time PCR. Other reporter constructs with or without a quencher moiety may also be used.

The inventive methods can be used to assess the methylation status of multiple genes, using very small quantities of DNA. A cumulative score of hypermethylation among multiple genes better distinguishes normal or benign from malignant tumors in bodily fluid samples as compared to the value of individual gene methylation markers. Using the cMethDNA methods of the present invention it is possible to objectively define the range of normal/abnormal DNA sequence hypermethylation in a manner that is translatable to a larger clinical setting (FIG. 4). The inventive methods may also be used to examine cumulative hypermethylation in benign conditions and as a predictor of conditions, such as various cancers and their metastases that are associated with DNA hypermethylation. The inventive methods may also predict conditions not associated with cancers, such as pre-eclampsia or eclampsia, viral disease (e.g. herpes virus, hepatitis B virus), neurodegenerative and psychiatric disorders.

In accordance with an embodiment, the primer extension reaction is a linear amplification reaction, wherein the primer extension reaction is performed over a number of cycles, and the linear amplification product that is generated is detected.

Due to the sensitivity of the inventive methods, the first amplification product is optionally diluted from about 1:5 to about 1:10$^5$ and optionally separate aliquots of the first amplification product are further subjected to cMethDNA as described herein.

In real-time PCR, as used in the inventive methods, one or more aliquots (usually dilute) of the first amplification product is amplified with at least a first primer of an internal amplification primer pair, which can selectively hybridize to one or more amplicon in the first amplification product, under conditions that, in the presence of a second primer of the internal amplification primer pair, and a fluorescent probe allows the generation of a second amplification product. Simultaneously, at least one or more internal primer pairs specific for the STDgene for the TARGETgene(s) of interest also can selectively hybridize the STDgene in the presence of a second fluorescent probe specific for the STDgene. Detection of fluorescence from the second amplification product(s) provides a means for real-time detection of the generation of a second amplification product and for calculation of the amount of methylated TARGETgene and associated STDgene.

It should be recognized that an amplification "primer pair" as the term is used herein requires what are commonly referred to as a forward primer and a reverse primer, which are selected using methods that are well known and routine and as described herein such that an amplification product can be generated therefrom.

As used herein, the phrase "conditions that allow generation of an amplification product" or of "conditions that allow generation of a linear amplification product" means that a sample in which the amplification reaction is being performed contains the necessary components for the amplification reaction to occur. Examples of such conditions are provided in Example 1 and include, for example, appropriate buffer capacity and pH, salt concentration, metal ion concentration if necessary for the particular polymerase, appropriate temperatures that allow for selective hybridization of the primer or primer pair to the template nucleic acid molecule, as well as appropriate cycling of temperatures that permit polymerase activity and melting of a primer or primer extension or amplification product from the template or, where relevant, from forming a secondary structure such as a stem-loop structure. Such conditions and methods for selecting such conditions are routine and well known in the art (see, for example, Innis et al., "PCR Strategies" (Academic Press 1995); Ausubel et al., "Short Protocols in Molecular Biology" 4th Edition (John Wiley and Sons, 1999); "A novel method for real time quantitative RT-PCR" Gibson U. E. et al. *Genome Res* (1996) 6:995-1001; "Real time quantitative PCR" Heid C. A. et al. *Genome Res* (1996) 6:986-994).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids used as primers in embodiments of the present invention can be constructed based on chemical synthesis and/or enzymatic ligation reactions using procedures known in the art. See, for example, Sambrook et al. (eds.), *Molecular Cloning, A Laboratory Manual*, 3$^{rd}$ Edition, Cold Spring Harbor Laboratory Press, New York (2001) and Ausubel et al., *Current Protocols in Molecular Biology*, Greene Publishing Associates and John Wiley & Sons, NY (1994). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The term "isolated and purified" as used herein means a protein that is essentially free of association with other proteins or polypeptides, e.g., as a naturally occurring protein that has been separated from cellular and other contaminants by the use of antibodies or other methods or as a purification product of a recombinant host cell culture.

The term "biologically active" as used herein means an enzyme or protein having structural, regulatory, or biochemical functions of a naturally occurring molecule.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

It will be understood by those of ordinary skill in the art that the methods of the present invention can be used to diagnose, prognose, and monitor treatment of any disease or biological state in which methylation of genes is correlative of such a disease or biological state in a subject. In some embodiments, the disease state is cancer.

In accordance with one or more embodiments of the present invention, it will be understood that the types of cancer diagnosis which may be made, using the methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream.

The cancer can be a metastatic cancer or a non-metastatic (e.g., localized) cancer, an invasive cancer or an in situ cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, staging, screening, or other patient management, including treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules.

As used herein, the term "selective hybridization" or "selectively hybridize" refers to hybridization under moderately stringent or highly stringent conditions such that a nucleotide sequence associates with a selected nucleotide sequence but not with unrelated nucleotide sequences. Generally, an oligonucleotide useful as a probe or primer that selectively hybridizes to a selected nucleotide sequence is at least about 15 nucleotides in length, usually at least about 18 nucleotides, and particularly about 20 nucleotides in length or more in length. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual" (Cold Spring Harbor Laboratory Press 1989)).

The phrase "a comparable normal DNA sample" as used herein means that the plurality of genomic DNA sequences that is being tested for methylation status, such as in a plant or insect, is matched with a panel of genomic DNA sequences of the same genes from a "normal" organism of the same species, family, and the like, for comparison purposes. For example, a substantial cumulative increase or decrease in the methylation level in the test sample as compared with the normal sample (e.g., the cumulative incidence of the tumor marker in a test DNA panel compared with that cumulatively found in comparable apparently normal sample) is a reliable indicator of the presence of the condition being assayed.

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

As used herein the term "optically detectable DNA probe" means an oligonucleotide probe that can act as a molecular beacon or an oligonucleotide probe comprising a fluorescent moiety or other detectable label, with or without a quencher moiety.

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

In accordance with another embodiment of the present invention, it will be understood that the term "biological sample" or "biological fluid" includes, but is not limited to, any quantity of a substance from a living or formerly living patient or mammal. Such substances include, but are not limited to, blood, serum, plasma, urine, cells, organs, tissues, bone, bone marrow, lymph, lymph nodes, synovial tissue, chondrocytes, synovial macrophages, endothelial cells, and skin. In a preferred embodiment, the fluid is blood or serum.

In an embodiment, the inventive methods are illustrated using primary breast cancer as an example. In breast cancer, samples can be collected from such tissue sources as ductal lavage and nipple aspirate fluid where the DNA amount is limiting, for example as little as about 50 to about 100 cells, as well as in larger samples, such as formalin-fixed paraffin-embedded sections of core biopsies. The maximum input DNA is approximately 600 ng. Using invention methods of cMethDNA, the level and incidence of hypermethylation CpG islands in AKR1B1, ARHGEF7, COL6A2, GPX7, HIST1H3C, HOXB4, MAL, RASGRF2, RASSF1A, TM6SF1, TMEFF2, TWIST1, ALX1, DAB1, DAB2IP, GAS7C, GSTP1, HIN1, HIC1, and RARB2, genes in samples where DNA is limiting or when extreme sensitivity is desired can be co-amplified for the purpose of detecting progression of primary breast cancer in a subject. Scoring the cumulative methylation of these gene regions within a sample gives high sensitivity and specificity of detection of primary breast cancer and a global indication of promoter hypermethylation in tumors relative to normal tissue. The invention methods are designed to evaluate samples that contain extremely limited amounts of DNA, such as those from ductal lavage or nipple aspiration. In the process, the extent of gene hypermethylation in primary breast cancer has been evaluated and the method is readily adaptable to clinical testing. Although this technique is illustrated with respect to breast tissues, the technique can be used to evaluate gene (e.g., gene promoter) hypermethylation within a wide range of tissues.

cMethDNA can be performed in an individual microtube, a 96 well platform as well as in a 384 well platform or larger and can be used for high throughput if cMethDNA is formatted for a larger setting, such as digital PCR. The cMethDNA technique is applicable to fresh or frozen ductal lavage material, plasma, blood, serum, nipple aspiration fluid, CSF, and fine needle aspirates. Other sources of sample DNA are also suitable for cMethDNA monitoring including but not limited to bronchial washings, buccal cavity washings, prostatic fluids, and urine. Conditions that are unrelated to cancer which are suitable for monitoring by the invention include but are not limited to eclampsia and pre-eclampsia.

More informative than evaluating the methylation status of a single gene, studies of cumulative multi-gene promoter hypermethylation indicated that striking differences exist between normal and malignant tissues (FIGS. 2-4).

The present invention also provides kits for screening methylation of genes or therapeutic applications. For screening applications, such kits may include any or all of the following: assay reagents, buffers, and for each TARGETgene the cMethDNA kit includes: 1) external primers, forward and reverse, 2) TARGETgene methylation status-specific internal primers, forward and reverse, 3) STDgene-specific internal primers, forward and reverse, 4) probes to match #2 and #3, individually in distinct colors (e.g., 6FAM/TAMRA or VIC/TAMRA, or other combinations), or the like.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

Patients and Blood Collection for Assay Development. Whole blood was collected at Johns Hopkins, Baltimore Md. from women with metastatic breast carcinoma at the time of diagnosis of disease recurrence, as well as from healthy controls. All samples were collected with appropriate approval from the institutional review board.

Method for processing of cell-free serum DNA for methylation array. Whole blood was collected in an SST Vacutainer tube (BD Diagnostics, Franklin Lakes, N.J.; #367988), allowed to clot and separated according to manufacturer's directions within 2 hours. Serum (6 ml) was digested overnight at 48° C. by inverting continuously with 12 ml buffer containing 1% SDS, 100 mM Tris pH 8.5, 2.5 mM EDTA, and 120 µl 2% w/v proteinase K (Roche Applied Sciences, Indianapolis, Ind.). Thereafter, three times daily 120 µl 2% proteinase K was added for a total of 72 hours of digestion. The sample was centrifuged 10 minutes and supernatant was extracted in an equal volume of warm (50° C.) Tris buffer-saturated phenol/chloroform pH 8.0. Phase Lock Heavy Gel (5 Prime, Gaithersburg, Md.) was used to isolate the aqueous layer. DNA was precipitated with ethanol in the presence of glycogen and NaCl, washed in 70% ethanol, and resuspended in 1 mM Tris, pH 8. Sodium bisulfite conversion was performed using EZ DNA Methylation kit (Zymo Research, Orange, Calif., USA) as directed by the manufacturer. Eluted DNA was processed with the Illumina Infinium HumanMethylation27 BeadChip (Illumina, Inc., San Diego, Calif.; WG-311-1202) in the JHU DNA Microarray Core. GenomeStudio software (Illumina) was used to analyze array results. Methylation levels were defined according to the manufacturer, as 1-values (similar to % methylation) ranging from 0-1 (low to high, respectively). DiffScores were computed after Benjamini and Hochberg correction for false discovery (p=0.05). The Diff Score is a transformation of the p-value that provides directionality to the β-value based on the difference between the average signal in the reference group vs. the comparison group. The formula is: DiffScore=10*sgn(µcond−µref)*log 10p; For a p-value of 0.05, DiffScore=±13; For a p-value of 0.01, DiffScore=±22; For a p-value of 0.001, DiffScore=±33; p=10'(DiffScore*sgn(µcond−µref)/10).

Methylation Array Analysis. Six ml serum from women with metastatic breast cancer or healthy volunteers was digested with proteinase K, DNA extracted, and bisulfite treated (EZ DNA Methylation kit, Zymo Research, Orange, Calif.) as directed. Bisulfite-converted DNA was processed for the Infinium HumanMethylation27 BeadChip (Illumina, Inc., San Diego, Calif.; WG-311-1202). Methylation was measured as β-value, ranging from 0-1 (low to high, respectively). Differential methylation analyses were accomplished using GenomeStudio (Illumina). Data have been deposited with the Gene Expression Omnibus (GEO) repository.

Purification of Cell-free Circulating DNA. External gene-specific standards (50 copies TARGETgene per gene of interest. In this example, 12 genes of interest were used) and carrier DNA/RNA (1 µg salmon-sperm and 3 µg tRNA)

were added to each serum sample (300 µl), and cell-free DNA was extracted. Three serum DNA purification kits were evaluated: QiaAmp MiniElute Virus Spin Kit (ME; Qiagen, Valencia, Calif.), QiaAmp UltraSens Virus Kit (US; Qiagen), and Quick-gDNA MiniPrep (ZR; Zymo Research, Orange, Calif.). Extracted DNA was modified with sodium bisulfite, column-purified and eluted in 15 µl water according to the manufacturer's protocol.

Processing of Serum DNA for cMethDNA Assay. Serum was purified using the MiniElute Virus Spin Kit (Qiagen catalog #57704), essentially according to the manufacturer's protocol although modified for cMethDNA. For each new kit, stocks were prepared of protease (1.4 ml AVE to protease vial, mix, aliquot and store at −20° C.), and of carrier RNA (310 µl AVE in 310 µg carrier RNA, dissolve, freeze at −20° C. in aliquots @1 µg/ml; use 5.6 µg/sample). All steps were performed at room temperature, including centrifugation; Buffer AVE was equilibrated to room temperature for the elution step; an incubator oven was pre-warmed to 56° C.; a working dilution of carrier RNA was prepared (per sample=294 µl Buffer AL+5.6 µl carrier RNA in Buffer AVE). The following protocol was then performed: About 37 µl Qiagen Protease (prepared in AVE and stored in −20° C. freezer) was transferred into a 2 ml microcentrifuge tube, and about 300 µl serum was added and mixed. About 300 µl of Buffer AL containing 5.6 µg of carrier RNA (5.6 µl) was then added and mixed. Immediately before using, the frozen stock STDgene cocktail was thawed and about 2 µl of STDgene stock $10^3$/µl with 198 µl dilution buffer (IX MSP buffer, 50 µg/ml tRNA, 50 µg/ml salmon sperm DNA) was mixed. About 5 µl of the diluted STDgene cocktail is then added to the serum dilution. In the present example 12 unique STDgenes, 50 copies total of each STDgene were present in the final serum mixture. This was then mixed and incubated at 56° C. for about 15 minutes in a pre-warmed rack and then briefly centrifuged. About 375 µl absolute ethanol is added and mixed by pulse-vortexing for 15 seconds. The lysate is incubated with the ethanol for 5 minutes at room temperature (not to exceed 25° C.) and then briefly centrifuged. All the lysate is then transferred onto the QIAamp MinElute column and centrifuged at 8000 rpm for about a minute and then transferred to a new collection tube with the filtrate discarded. The column is washed with 500 µl Buffer AW1, centrifuged at 8000 rpm for 1 minute and transferred to a new collection tube. The column is washed with 500 µl Buffer AW2 and centrifuged at 8000 rpm for about a minute and then transferred to a new collection tube. The column is washed with 500 µl absolute ethanol centrifuged at 8000 rpm for 1 minute and transferred to a new collection tube. The empty column is centrifuged at full speed (13,000 rpm) for about 3 minutes and transferred to a new collection tube. About 22 µl Buffer AVE is added directly to the center of the membrane and incubated at room temperature for about 5 minutes and then centrifuged at full speed 1 minute and repeated and pooled. The contents are transferred to a 500 µl microcentrifuge tube for sodium bisulfite treatment and kept on ice.

Sodium Bisulfite-Mediated Conversion of Serum DNA. About 7.5 µl M-dilution buffer (Zymo Research) is added to the DNA sample (volume is ~50 µl), and incubated at 42° C. for 20-30 minutes, then briefly centrifuged. After preparing the CT Conversion Reagent (for each sample: water=71.4 µl, M-dilution buffer=17.6 µl, CT granular conversion reagent (Zymo Research)=54 mg; add about 750 µl ddH$_2$O and 185 µl M-dilution buffer to the 1.7 ml brown vial containing 567 mg of CT reagent, which is enough for 11 serum DNA samples. The solution is rotated in the dark at room temp for 10 minutes to dissolve. About 97.5 µl of CT Conversion Reagent is mixed with the sample thoroughly, and vortexed briefly with a final volume of about 150 µl. The DNA solution is incubated in a PCR machine with a hot lid cycling 16 cycles of (95° C. 30 seconds, 50° C. 1 hour). The solution is held at 4° C. and briefly centrifuged. The DNA was cleaned up with 600 µl of M-Binding Buffer (Zymo Research) using a Zymo Spin Column (IC) in a collection tube and centrifuged at 13000 rpm for 30 seconds and change to a new collection tube, washed with M-Wash Buffer (Zymo Research) and centrifuged at 13000 rpm for 30 seconds. 200 µl M-Desulfonation Buffer (Zymo Research) was added to the column and let the mixture sit at room temperature for 30 minutes, then centrifuged at 13000 rpm for 30 seconds and repeated. The column was transferred to a new collection tube, 15 µl of 70° C. water was added to the column, and allowed to sit for 5-10 minutes at room temperature, followed by centrifugation to recover the DNA. The sample was placed on ice and then used to perform multiplex PCR using the entire sample.

The cMethDNA Assay. The cMethDNA assay primers/probes were designed in close proximity (100 bp) to the methylated array locus identified by array analysis. The cMethDNA assay primers (two) and probe (one) jointly contain about 9-11 CpG dinucleotides (ranging from 7-12) depending on the desired melting temperatures of the primers/probe and the density of CG dinucleotides in the region; independent C residues (about 8; ranging from 6-10) are also present to insure selective hybridization only to sodium bisulfite-converted DNA. The cMethDNA assay sets included: 1) A set of gene-specific reference DNAs (STDgene) of the same size as the gene of interest that have identical 5' and 3' ends as each endogenous DNA target gene of interest (TARGETgene) and internal lambda phage sequences (unique to each standard type), 2) one pair of external primers (forward and reverse) that can hybridize to both TARGETgene and STDgene DNA independent of DNA methylation, 3) one pair of methylation-specific gene-specific internal primers for the TARGETgene of interest, forward and reverse, 4) one pair of STDgene internal primers, forward and reverse, and 5) probes which can hybridize to TARGETgene and STDgene DNA individually and in distinguishable colors (e.g., 6FAM/TAMRA or VIC/TAMRA).

Two sequential PCR reactions were performed. cMethDNA PCR reaction #1 (Multiplex Reaction): In the multiplex reaction DNA was amplified using "external" primers specific to sequences flanking the methylated region of interest. In this example, up to 12 genes per 50 µl reaction were co-amplified from ≥150 µg DNA template (50 copies of genomic DNA). The DNA yielded from 300 µl serum containing 50 copies of standard DNA was processed after bisulfite conversion.

The final 50 µl reaction was performed in 16.6 mM NH$_4$SO$_4$, 67 mM Tris pH 8.8, 6.7 mM MgCl$_2$, 1.25 mM dNTP (each; Denville Scientific, Metuchen, N.J.), 10 mM β-mercaptoethanol, 0.1% DMSO, 2 ng/ul of each primer and 10 U/50 µl Platinum Taq polymerase (Invitrogen). Thermocycler settings were 95° C. for 5 minutes, followed by 26 cycles of 95° C. for 30 seconds, 56° C. for 45 seconds, and 72° C. for 45 seconds, then a final extension of 7 minutes at 72° C. After completion of PCR, the reaction mix was diluted 1:5 by adding 200 µl 1× Multiplex Dilution Buffer [containing 1×MSP buffer, 50 µg/ml Salmon Sperm DNA (Invitrogen), 50 µg/ml tRNA (Roche Applied Science, Indianapolis, Ind.)] before performing the quantitative real-time PCR assay. The reaction mix was stored frozen at −20° C.

TABLE 2

Reaction Conditions for PCR reaction #1

| FINAL CONCENTRATION | MULTIPLEX: PCR #1 | 1X |
|---|---|---|
| 1X | 10 × MSP Buffer | 5.0 µl |
| — | ddH$_2$0 | 4.5 µl |
| 1.25 mM | 25 mM dNTP (Denville Scientific; 100 mM dNTP Master mix) | 2.5 µl |
| 10 U | Platinum Taq (5 U/µl; Invitrogen) | 2.0 µl |
| 2 ng per gene | 100 ng/ul Forward primer (1 µl each gene) | 1.0 µl/gene × 12 genes |
| 2 ng per gene | 100 ng/ul Reverse primer (1 µl each gene) | 1.0 µl/gene × 12 genes |
| | ddH$_2$0 (24.0 µl H$_2$0 - X µl primers) | 0 µl |
| 0.07-20 ng | DNA (eluted bisulfite-treated genomic DNA) | 12.0 µl |
| | TOTAL | 50.0 µl | cMethDNA PCR reaction #2 (Real-time Reaction): For the real-time PCR reaction, the amplicons from Reaction #1 were quantified using two-color real-time PCR, according to the absolute quantitation method. Each TARGETgene and its paired reference STDgene were assayed independently, but in the same well. Controls were used in each reaction to insure specific hybridization to target or reference, as well as the absence of contamination. For cMethDNA the Methylation Index (MI) was calculated for each gene using the formula $$MIgene = \frac{Mgene \text{ copies}}{\text{Total}(Mgene + STD \text{ gene}) \text{copies}}(100).$$

The cumulative methylation index (CMI) was calculated as the sum of MI for all genes.

The real-time PCR reaction was performed in 20 µl containing 16.6 mM NH4SO4, 67 mM Tris pH 8.8, 6.7 mM MgCl2, 10 mM β-mercaptoethanol, 0.1% DMSO, 300 nM ROX (Invitrogen/Life Technologies, Grand Island, MY), 200 µM dNTP (Denville Scientific), 10 µg/ml tRNA (Roche Applied Science, Indianapolis, Ind.), 1.0 U RAMP Taq polymerase (Denville Scientific; #CB4080-9), 800 mM each forward and reverse primer (Life Technologies/Foster City, Calif.), and 200 nM for each hydrolysis probe (labeled with 6FAM/TAMRA or VIC/TAMRA; Applied Biosystems/Life Technologies).

For each sample or multiplex reaction control 4 µl was tested at a final 1:500 or 1:50,000 dilution (diluted in IX MSP dilution buffer. 16.6 mM NH$_4$SO$_4$, 67 mM Tris pH 8.8, 6.7 mM MgCl$_2$, 10 mM β-mercaptoethanol, 0.1% DMSO, 50 µg/ml salmon sperm, 50 µg/ml tRNA).

To prepare a standard curve for each gene, aliquots of stock were prepared containing equal copy number of TARGETgene and STDgene (as determined by overlapping amplification plots in real-time PCR). For each assay the curve DNA was serially diluted 1:10 for 7 logs into salmon sperm DNA (50 µg/ml), then discarded after use. Four microliters was assayed in duplicate wells by real-time. To make the stocks of the curve DNA, TARGETgene and STDgene templates were amplified independently for each gene using the multiplex PCR reaction protocol, 10 ng template DNA (either universally methylated DNA made by SssI treatment of cell line DNA, or plasmid DNA containing standard), using 4 ng forward and reverse primers. These stocks were stored at −80° C. and are stable indefinitely.

Absolute quantitation of multiplex amplicons was performed using ABI 7500 software according to instructions from manufacturer, with several modifications. While the automatic baseline setting was used, the threshold was set manually to the same setting for all samples, TARGETgene or STDgene (e.g. usually ΔRn between 0.02 and 0.04), then standard curve serial dilutions were assigned copy number values beginning with 200,000,000 copies/well for the most concentrated points. Sample values were extrapolated from the curve for target and reference DNAs and only sample values falling within the range of the standard curve were accepted. The Methylation Index (MI) for each gene was calculated as described above.

If ideal overlap of the TARGETgene and STDgene DNA curves was not obtained, and if the average ΔCt was <1.0 cycle, the curve was accepted and then the copy number was back-calculated in this way: 1) Based on the average ΔCt for all points of the curve (7 logs) the fold-difference (Δ1 cycle=2-fold) was calculated. 2) The value of the most concentrated sample was divided by this difference. Example: If the ΔC$_t$ STDgene−TARGETgene=1.5 cycles, then $2^{1.5}$=2.828, and 200,000,000 copies/2.828 fold=70,700,000 copies. Assign STDgene=70,700,000 and TARGETgene=200,000,000 copies per well.

TABLE 3

Reaction Conditions for PCR Reaction #2

| FINAL CONCENTRATION | REAL-TIME MSP: PCR #2 | 1X |
|---|---|---|
| 1X | 10 × MSP Buffer | 2.0 µl |
| — | ddH$_2$0 | 0.42 µl |
| 200 µM | 25 mM dNTP (Denville Scientific; 100 mM dNTP Master mix) | 0.16 µl |
| 50 µg/ml | tRNA (10 mg/ml) | 0.10 µl |
| 300 nM | ROX 50X (Invitrogen; 25 µM) | 0.24 µl |
| 1.0 U | RAMP TAQ (5 u/µl; Denville Scientific) | 0.20 µl |
| 800 nM | 5 µM Forward primer (TARGETgene) | 3.2 µl |
| 800 nM | 5 µM Reverse primer (TARGETgene) | 3.2 µl |
| 200 nM | 100 µM Probe (FAM-TARGETgene) | 0.04 µl |
| 800 nM | 5 µM Forward primer (STANDARDgene) | 3.2 µl |
| 800 nM | 5 µM Reverse primer (STANDARDgene) | 3.2 µl |
| 200 nM | 100 µM Probe (VIC-STANDARDgene) | 0.04 µl |
| | DNA (diluted from multiplex reaction) | 4.0 µl |
| | TOTAL | 20.0 µl |

An Applied Biosystems (ABI) MicroAmp Fast Optical 96 Well Plate (#4346906) was used with the ABI Fast 7500 Real-Time PCR System. Usually the standard curve samples were placed in Row A wells 1-12, and in Row B wells 1-2. Row B well 3 contained NTC (no template control) from the multiplex reaction, well 4 contained NTC from the real-time reaction mix, well 5 contained STD cocktail (no target DNA) from the multiplex, and well 6 contained universally methylated genomic DNA (no STD reference DNA). The remaining wells were occupied by samples.

Statistical Analysis. Methylation array analyses were performed within GenomeStudio software (Illumina). Probe detection p-values were calculated using GenomeStudio. DiffScore was computed by GenomeStudio after Benjamini and Hochberg correction for false discovery. cMethDNA data analyses were performed using GraphPad Prism version 5.0 (GraphPad Software, San Diego, Calif.). Box and Whiskers plots were analyzed by Mann-Whitney test. Receiver Operating Characteristic (ROC) curve analyses were used to define a laboratory threshold maximizing sensitivity and specificity in the training set. The significance of pre- and post-treatment methylation levels was analyzed using the Wilcoxon signed rank test.

Example 1

Recently, genome wide-DNA methylation arrays and bisulfite treated DNA sequencing of primary breast tumors have resulted in the identification of novel subgroups from the "intrinsic subtypes" identified by gene expression profiling (Breast Cancer Res. 2007; 9:R20; Pathobiology. 2008; 75:149-52; Anal Cell Pathol (Amst). 2010; 33:133-41; Cancer Epidemiol Biomarkers Prev. 2007; 16:1812-21; J Epidemiol. 2012; 22:384-94). As a first step to comprehensively analyze the methylation profile of circulating DNA in breast cancer patients, a methylation array analysis was conducted using the Infinium HumanMethylation27 BeadChip Array (Illumina, Inc.) on a discovery set of six recurrent metastatic breast cancer sera, five normal sera, and twenty normal leukocyte (four pools of 5 individuals each) (Table 1). An unsupervised hierarchical cluster analysis performed using 26759 probes (97% of the array; probe detection p-values <0.0001) found that cancer and normal sera clustered into two separate groups, indicating the presence of unique profiles of genomic methylation (FIG. 1A). To identify loci exhibiting frequent, cancer specific methylation changes, cancer sera were compared to normal according to the schema outlined in FIG. 1B. Probes were selected with: 1) the most reproducible performance in all individual samples (cancer and normal serum; probe detection p-value <0.00001; 97%, 26759/27578 probes), 2) ≥2-fold more methylation in serum from cancer versus normal controls (902/26759 probes), 3) ≥1.5-fold more methylation in tissues from breast cancer (n=89) versus normal controls (n=21) tissue, data from our previous study (11), and leukocyte DNA (n=4 pools) (232/902 probes), 4) low methylation (≤0.15 β-value methylation) in individual normal serum samples (n=5) and individual normal breast tissue samples (n=15) (172 probes) and finally, to optimize sensitivity across all methylation subtypes of breast cancer, we selected 13 gene promoter located markers that were methylated in 30% or more of the breast cancers in our database. The 172 cancer-specific CpG probes were subjected to a supervised hierarchical analysis; this distinguished cancer from normal serum and leukocyte DNA samples (data not shown). Scatter plots in FIG. 1C (left panel) show average beta methylation values of the 172 probes in normal serum versus cancer serum and on FIG. 1C (right panel), cancer tissues versus normal breast; pink dots indicate location of the 13 genes selected for verification, described in Table 1. In the scatter plots, ±1.5 fold levels are indicated by red lines, central line indicating identical methylation levels.

Seven of the 13 probes selected were also those present in our previously identified candidate recurrence markers (AKR1B1, ALX1, COL6A2, GPX7, HOXB4, RASGRF2, TM6SF), associated with poor outcome in breast cancer, lending strength to the possibility that these markers lend biological import to the metastatic process. Methylation beta values and frequency of the 13 probes was then verified individually in the patient (n=5) and normal serum (n=6) DNA samples used for arraying (data not shown). It was observed that these probes were differentially hypermethylated with varying frequency in the metastatic patient sera compared to normal, and as a panel were likely to provide a pan methylation marker panel for breast cancer.

Example 2

Marker detection frequency in circulating tumor DNA. In this example, fourteen genes hypermethylated in cancer sera compared to normal were tested-thirteen novel genes (HOXB4 miRNA, RASGRF2, ARHGEF7, AKR1B1, TMEFF2, TM6SF1, COL6A2, GPX7, HIST1H3C, ALX1, DAB1, DABIP2, and GAS7) identified by array analysis and RASSF1A, based upon our prior experience. Methylation frequency of the 14 genes was then verified in the patient and normal serum DNA samples used for arraying with the cMethDNA assay. The gene panel was refined by removing genes from the panel with high background or low frequency (FIG. 2B), specifically eliminating ALX1, DABIP2, and DAB1 which displayed levels of methylation of above 7 units (the set threshold for "normal" in normal control serum), and eliminating GAS7 based on its low methylation frequency (less than 20%) in cancer sera. Next, the finalized ten-gene panel was evaluated in a training set of samples (n=52, Table S5). As shown in FIG. 2C, statistical evaluation showed that cumulative methylation levels were consistently high in patients with metastatic breast cancer, and negligible in women without cancer (median CMI=117.3 and 0.04, respectively; p<0.0001, Mann Whitney).

Example 3

Figure 3A:
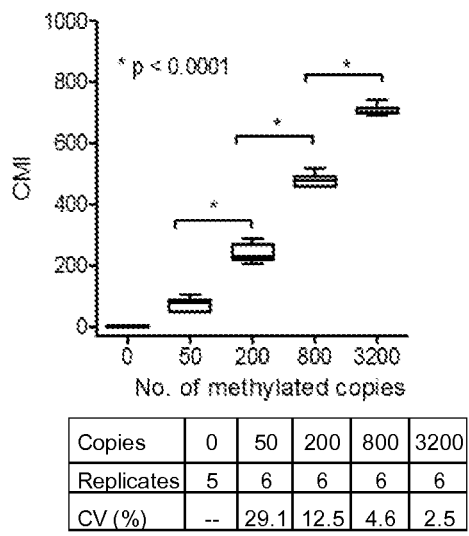
FIG. 3 depicts steps to assay validation. 3A) Reproducibility of cMethDNA assay in six replicates group of samples of normal serum spiked with 0 to 3200 copies of methylated genomic MDA-MB-453 DNA. Box-Whisker plots show the median and range of CMI (Y-axis) for replicates of each sample (X-axis). Statistical significance (Mann-Whitney test) and p values are indicated, and a table provides details and % coefficient of variation (CV, a normalized measure of frequency distribution) for each test. 3B) Comparison of cMethDNA and QM-MSP assays. cMethDNA had significantly higher cumulative methylation levels in replicates at each of the copy numbers (p=0.0022-0.005). 3C) QM-MSP and cMethDNA methods were directly compared to each other on aliquots of multiplexed serum DNA from each of twelve independent metastatic breast cancer patient serum samples. By using gene-specific standards as qPCR reference, cMethDNA yielded significantly higher RASSF1A methylation values compared to the QM-MSP method, using gene-specific unmethylated DNAs as reference (p=0.0233, paired t-test). 3D) Inter-user reproducibility evaluated for a set of thirteen patient serum samples by two independent investigators within the same laboratory. User performance evaluated for the 10-gene panel, using the intra-class correlation coefficient indicates high reproducibility (0.99; 95% CI 0.96-1.00).
Figure 3B:
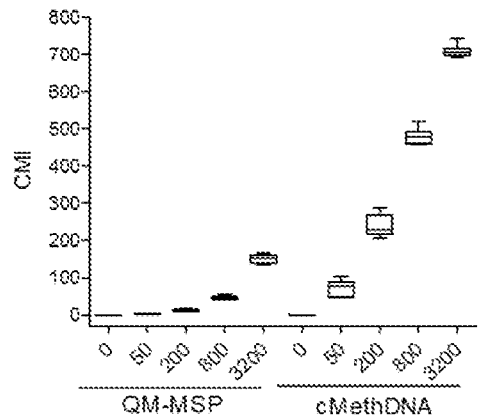
Figure 3C:
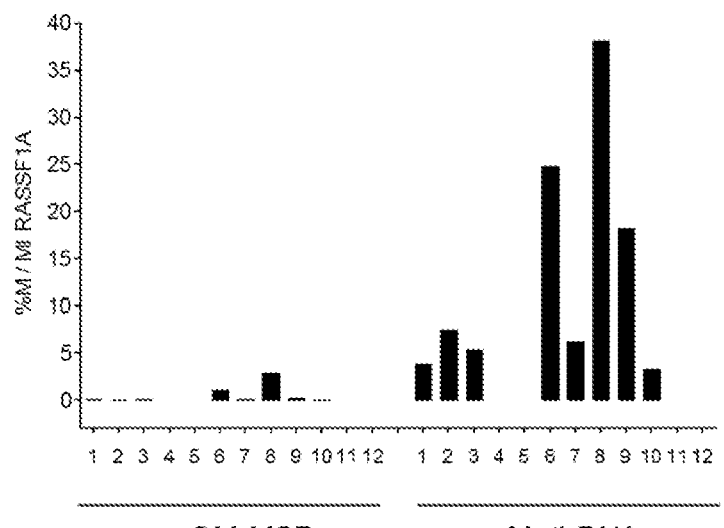
Figure 3D:
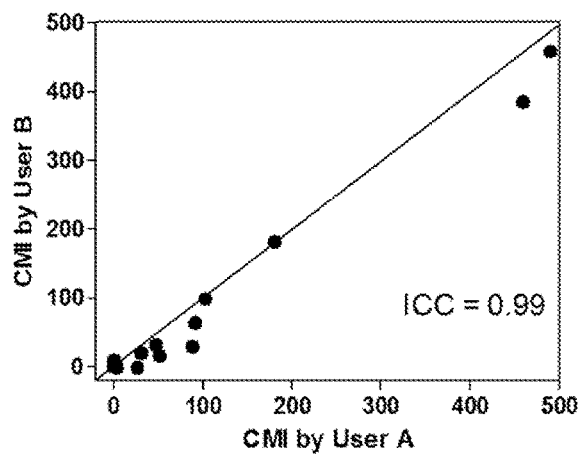

Technical evaluation of the cMethDNA assay, Analytical linearity and sensitivity. To establish assay linearity and sensitivity, a series of experiments were performed. An optimal procedure was established for isolating minute amounts of circulating DNA by testing three different serum DNA extraction methods (UltraSens Virus Kit, Qiagen; MiniElute Virus Kit, Qiagen, and Quick-gDNA Prep Zymo Research). A master mix of serum from a single normal donor (300 µl serum per assay point) was spiked with a physiological range (0, 50, 200, 800 or 3200 copies) of fully methylated DNA extracted from the MDA-MB-453 breast cancer cell line. The coefficient of variation for each replicate (5-6 replicates) was calculated for each method (FIG. 3A). The lowest level of 50 copies of spiked genomic DNA was detectable by all three methods, and negligible levels of methylated DNA were observed in the normal sera. However, of the three kits tested (FIG. 3A), the MiniElute Virus Spin Kit method displayed highest reproducibility, as judged by the smallest inter-assay coefficients of variation (CV=29%, 12%, 4.6%, 2.5%, for 50, 200, 800 or 3200 methylated DNA copies, respectively), and all levels of spiked DNA amplified for every gene in each of the six assays. It will be understood by those of ordinary skill in the art that any of the DNA extraction methods known in the art can be used with the methods of the present invention.

Example 4

Figure 4A:
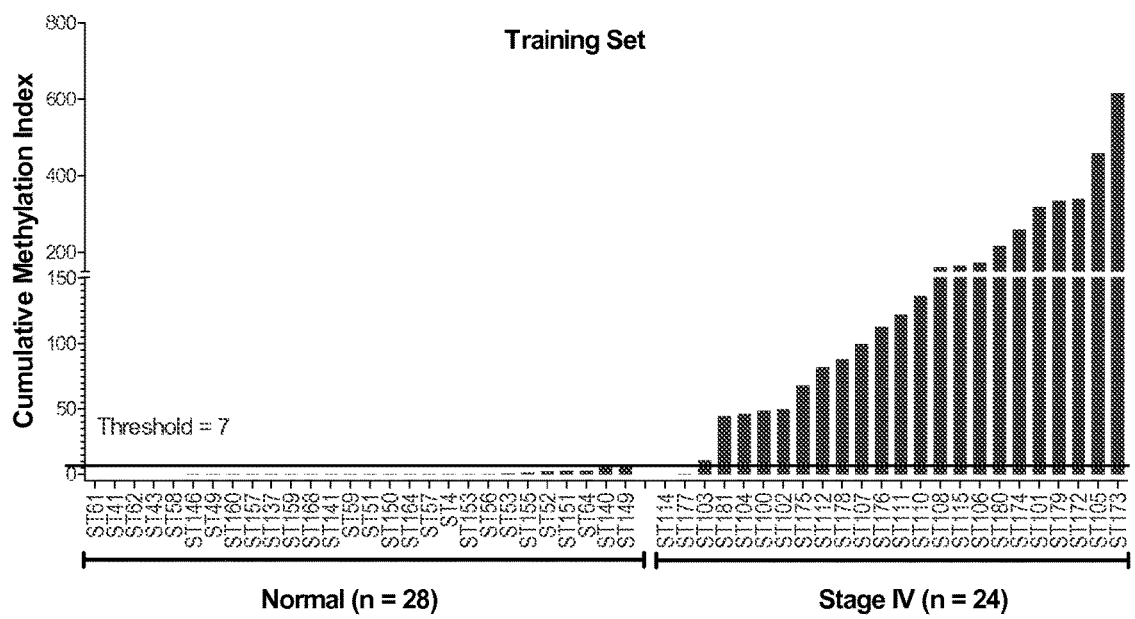
FIG. 4 shows detection of metastatic breast cancer DNA by cMethDNA. Serum samples from patients with recurrent metastatic stage IV disease were assigned to training and test sets (X-axis; from J0425/J0214 and J0524 trials, respectively, FIGS. 4A-4B). Serum samples from normal women were randomly assigned to each set. cMethDNA was performed on each set. A laboratory threshold (CMI=7 units; Y-axis) was defined by Receiver Operator Characteristic using the training set. The CMI (Y-axis; indicated by bar height) was calculated for the entire panel. 4C) Statistical analyses of these data are shown. 4D) The methylation frequency of individual markers in the panel (methylated defined as MI >1 unit).

Intra-Assay Testing. The cMethDNA assay is a refinement of the QM-MSP method invented in our laboratory and used extensively by our laboratory and others. In contrast to spiked standards added to serum to serve as an internal reference control in the cMethDNA assay, QM-MSP uses the free circulating unmethylated DNA of each gene as an internal reference. To demonstrate the improvement in sensitivity of cancer detection in the cMethDNA assay vs. the QM-MSP method, aliquots of the multiplexed reactions derived from 50-3200 copies of spiked DNA (shown in FIG. 4A) were tested in parallel by both methods (FIG. 4B). Cumulative methylation levels were significantly higher for cMethDNA at all levels of spiked methylated DNA (50 copies, p=0.0047; 200 copies, p=0.0048; 800 copies, p=0.005; 3200 copies, p=0.0022, Mann-Whitney). To confirm these findings in patient samples, sera from recurrent metastatic breast cancer patients were tested in parallel by cMethDNA and QM-MSP for methylated RASSF1A gene. Both signal magnitude and frequency of detection of hypermethylated RASSF1A was higher with cMethDNA compared to QM-MSP (p=0.0233, paired t-test) assay (FIG. 4C).

Example 5

Inter-Rater Reproducibility. cMethDNA assay values obtained by two users were compared after testing cancer sera (n=13) that were purified and assayed independently by each user. The inter-rater reproducibility evaluated using the intra-class correlation coefficient (0.99; 95% CI 0.96-1.00) showed a high level of reproducibility between users (FIG. 4D).

Example 6

Figure 5A:
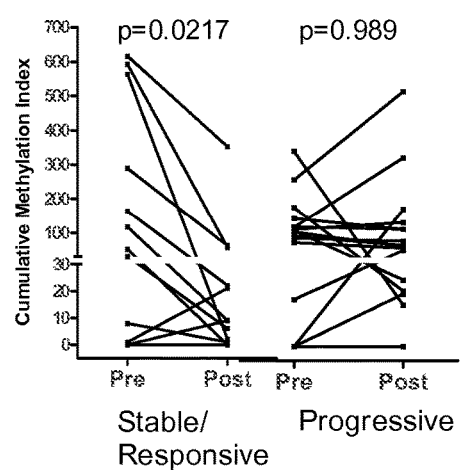
FIG. 5 depicts monitoring of treatment response. 5A) cMethDNA was performed on serum samples obtained from breast cancer patients (n=28) at the time of relapse with metastatic disease (Pre) and after 8-21 days of therapy (Post), 6-10 weeks prior to clinical evaluation of response. Data are plotted according to CMI in individual patients judged to have progressive disease or not, according to RECIST criteria after 8-12 weeks. 5B) The same data is plotted according to the percentage of change in CMI. 5C) (a-d): Representative plots of CMI of patient (ST#) sera assessed by cMethDNA at different time points during the course of treatment. a-b: 28 day cycles, c-d: 21 day cycles of chemotherapy. C: cycles of treatment; PD, SD: Imaging- and RECIST criteria-assessed progressive or stable disease respectively.
Figure 5B:
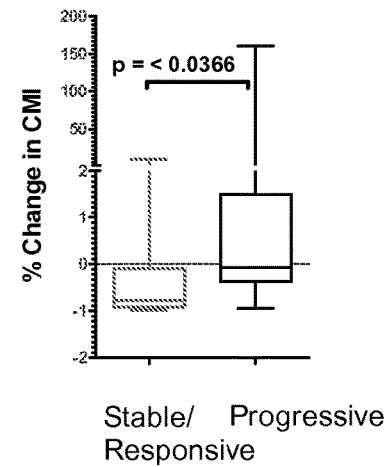
Figure 5C:
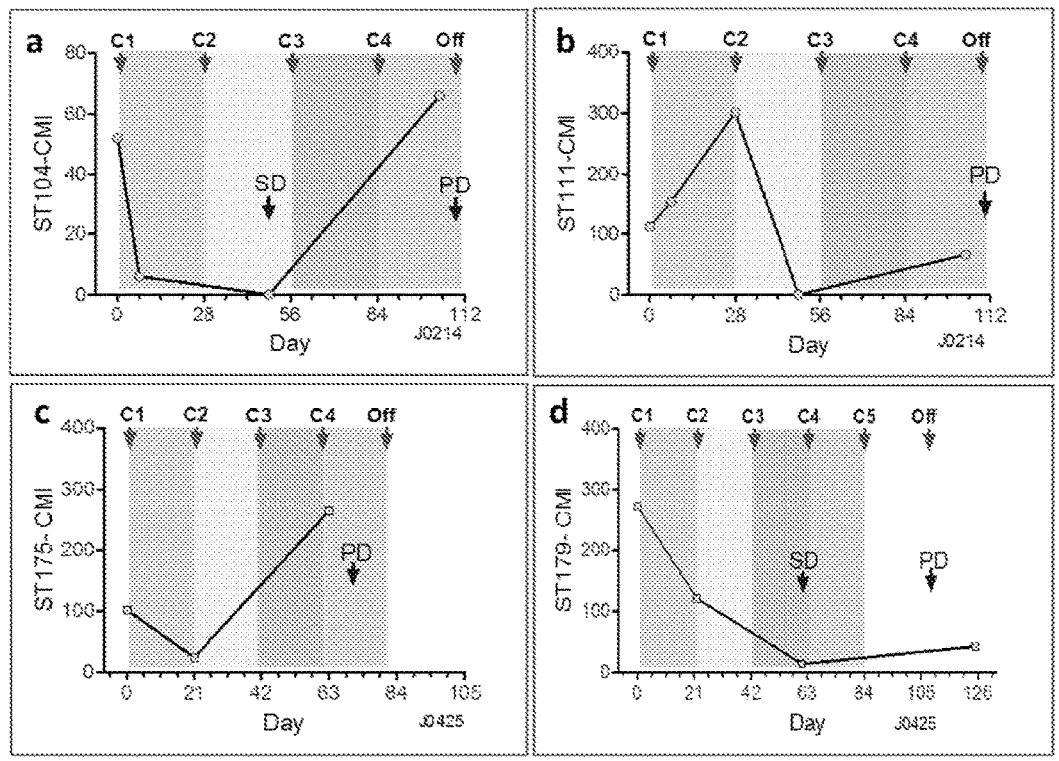

Detection of methylated DNA in serum of metastatic breast cancer patients-Assay Specificity. To establish a methylation threshold in normal serum in order to set optimal assay sensitivity and specificity criteria for metastatic breast cancer, a training set of 52 samples of sera consisting of patients with metastatic breast cancer (n=24) and women without cancer (n=28, mean age) was used. Receiver Operating Characteristic (ROC) analyses identified a threshold of 6.9 units with both maximum sensitivity and specificity in the patient training set; assay specificity was 96.4% (95% CI=81.7-99.9%), sensitivity was 91.7% (95% CI=73.0-99.0%), AUC=0.950 (95% CI=0.873-1.023; p<0.0001), the classification accuracy was 94% (49/52), and the likelihood ratio=25.7 (FIG. 5). In these samples, there was a high average frequency of methylation for any single gene (42%, ranging from 8-78%; FIG. 5). No age dependent change in methylation of the marker gene panel was observed in circulating free DNA in normal women (n=55), comparing youngest quartile to oldest among normal women using the unpaired t-test and correcting for unequal variances (p=0.643) or by one-way ANOVA among all four groups (p=0.8988)(data not shown).

Next, an independent test set of recurring metastatic breast cancer patient sera (n=33), and normal sera (n=27) was assayed using parameters defined in the training set (e.g. threshold). After locking the threshold at 7 units, the observed assay specificity was 100% (95% CI=87.2-100%), sensitivity was 90.9% (95% CI=75.7-98.1% p<0.0001), AUC=0.994 (95% CI=0.984-1.01%; p<0.0001), classification accuracy was 95% (57/60) and the likelihood ratio=24.6 (FIG. 5). Similar to the training set, the average frequency of methylation of individual genes was high (38.3%, ranging from 18%-67%); the gene with the highest incidence of methylation was RASSF1A. Thus, the cMethDNA assay of the present invention detected abnormal hypermethylation in serum with a high level of accuracy (of over 90%) in patients with metastatic breast cancer using novel markers discovered in serum by examination of 27K CpG sites represented in the methylation array.

Example 7

Utility of cMethDNA monitoring response to treatment. Previous studies have revealed the clinical significance of the circulating tumor cell (CTC) assay, not only in monitoring response to a new chemotherapy regimen but also to prognosticate long term outcome of the disease. Similarly, plasma or serum based assays for detecting circulating tumor antigens, tumor-specific DNA, mRNAs and proteins have been tested (J Natl Cancer Inst Monogr. 2011; 2011 (43):75-8). To determine if alterations in the CMI of our methylated gene marker panel as assessed by cMethDNA assay could be used to reflect response to chemotherapy, a pilot study was conducted on sera of patients with recurrent metastatic breast cancer. Patients (n=29) were staged prior to, and 6-12 weeks after treatment. Blood was collected before and at intervals during therapy. In all 29 patients, serum collected prior to initiation of treatment, and three weeks after initiation of a new chemotherapy regimen were tested by the cMethDNA assay.

In the total of 58 sera tested, which were collected at two time points, d1 of treatment, and at d8-12, the results showed that a statistically significant decrease in serum DNA methylation levels in patients with stable disease or a therapeutic response (p=0.001) but not in those progressive disease (p=0.728; Wilcoxon signed rank test). Using an ROC to select optimal sensitivity and specificity, a cutoff of −0.46% change distinguished progressing from non-progressing patients with a sensitivity of 89% and specificity of 91% (AUC=0.945, 95% CI 0.875-1.025, likelihood ratio 1.73). The data, although on a small sample set, shows the power of the cMethDNA assay of the present invention to reveal alterations that reflect response as determined at an early time point in the treatment schedule. Based on these findings, we performed an exploratory study to determine if changes in methylation levels reflected tumor burden during treatment. The cMethDNA assay was performed on sera from a subset of 16 patients for whom serum was available from three or more time points (total of 76 sera) collected during the different cycles of therapy.

Example 8

Patterns of methylation are retained between primary tumor and metastasis. In a previous study of DNA from primary tumor and distant metastasis collected at autopsy (performed with 4 hours of death), we observed a similarity in the methylation profile of the tumors at the primary site and the distant metastasis. It was hypothesized 1) that this multigene methylation pattern will be reflected in the serum as well and 2) may be useful to predict reappearance of metastasis prior to discovery by imaging and/or clinical examination. To test the first tenet of this hypothesis, we used the cMethDNA assay to test sets of primary tumor, and distant metastasis and serum collected soon after death collected from 10 patients. The age of the patients ranged from 33 to 79 years and the patients survived 2-11 years after diagnosis of their breast cancer. The results showed that there was a striking visual concordance between the methylated genes in the samples from the same patient (data not shown). Statistically, a high level of agreement was observed between serum and tissues, 50% of serum/tissue pairs were concordant for ≥9 markers, and none had fewer than 6 matches. Concordance observed between serum and tissue samples was similar to tissue to tissue comparisons. By chance alone, based on the overall frequency of the genes evaluated, the median number of matches predicted is 7 (range=3-9); the null distribution showed around 70% match rate. To strengthen these findings, a similar analysis was performed on primary tumor and blood collected upon diagnosis of recurrence, from ten patients in the training set, and a Stage 4 breast cancer cohort of 18 patients for whom biopsies of the primary tumor and concurrent distant metastasis tissue as well as blood was available. Here again, a striking similarity was observed of methylation pattern for the 10 gene panel tested by cMethDNA assay (data not shown). Further, this analysis revealed that in patients with Stage 4 breast cancer, methylated circulating DNA is detectable in 18/25 (72%) of the patients. These studies provide proof of principle that a core pattern of methylation is retained in the distant metastasis and serum of the same patient. The data also suggest that a comprehensive methylome analysis of the primary tumor of each patient at diagnosis, using the methods of the present invention, could likely provide a unique barcode or signature for that patient's cancer, and from other cancers arising in the same patient.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of quantifying the methylation of genes of interest (TARGETgenes) in a DNA-containing sample from a subject comprising:
   a) adding to the sample, a plurality of copies of a plurality of synthetic polynucleotide standards (STDgenes), wherein each different STDgene is specific for a different TARGETgene of interest, wherein each different STDgene comprises a DNA sequence having a similar number of nucleotides as the TARGETgene for which it is specific, wherein each different STDgene has 5' and 3' end nucleotide sequences which are homologous to nucleotide sequences of the TARGETgene for which it is specific, wherein the intervening DNA sequence between the 5' and 3' ends of each different STDgene lacks homology to the sequence of the TARGETgene for which it is specific or other human DNA; and wherein at least two different STDgenes are added to the sample;
   b) isolating and processing the DNA in the sample;
   c) preparing the DNA in b) for methylation-specific PCR via bisulfite treatment;
   d) amplifying the DNA in c) with at least two different external methylation-independent PCR primer pairs, where each different primer pair is capable of selectively hybridizing to a different TARGETgene of interest and also to the STDgene specific for that TARGETgene, using PCR under conditions sufficient to produce a first amplification product;
   e) obtaining a diluted sample of the first amplification product of d);
   f) for each different TARGETgene of interest, adding to e) one pair of internal methylation-dependent PCR primers specific for the TARGETgene of interest, one pair of internal PCR primers specific for the STDgene for the TARGETgene of interest, a unique optically detectable labeled DNA probe which specifically hybridizes to the TARGETgene of interest, and a unique optically detectable labeled DNA probe which specifically hybridizes to the STDgene for the TARGETgene of interest; and
   g) amplifying the DNA in f) using quantitative real-time PCR under conditions sufficient to produce a second amplification product which provides quantification of the amount of copies of (i) the methylated TARGETgenes of interest and (ii) the STDgenes for the TARGETgenes of interest.

2. The method of claim 1, wherein the quantification is used to calculate the degree of methylation of the TARGETgenes of interest using the formula:

(number of copies of the methylated TARGETgene of interest)/(number of copies of the methylated TARGETgene+number of copies of the STDgene of the TARGETgene of interest)×100.

3. The method of claim 1, further comprising the step of:
   h) comparing the amount of copies of each different methylated TARGETgene of interest from the sample to the amount of copies of the same methylated TARGETgene in a known control sample.

4. The method of claim 1, wherein at least one said optically detectable labeled DNA probe is a molecular beacon or an oligonucleotide probe comprising a fluorescent moiety with or without a quencher moiety.

5. The method of claim 1, wherein the subject is a mammal.

6. The method of claim 5, wherein the subject is a human.

7. The method of claim 1, wherein at least one TARGETgene of interest is selected from the group consisting of AKR1B1, ARHGEF7, COL6A2, GPX7, HIST1H3C, HOXB4, MAL, RASGRF2, RASSF1A, TM6SF1, TMEFF2, TWIST1, ALX1, DAB1, DAB2IP, GAS7C, GSTP1, HIN1, HIC1, and RARB2.

8. The method of claim 7, wherein the primers and probes are SEQ ID NOS: 1-12, SEQ ID NOS: 13-24, SEQ ID NOS: 25-36, SEQ ID NOS: 37-48, SEQ ID NOS: 49-60, SEQ ID NOS: 61-72, SEQ ID NOS: 73-84, SEQ ID NOS: 85-96, SEQ ID NOS: 97-108, SEQ ID NOS: 109-120, SEQ ID NOS: 121-132, SEQ ID NOS: 133-144, SEQ ID NOS: 145-156, SEQ ID NOS: 157-168, SEQ ID NOS: 169-180, SEQ ID NOS: 181-192, SEQ ID NOS: 193-204, SEQ ID NOS: 205-216, SEQ ID NOS: 217-228, or SEQ ID NOS: 229-240.

9. A method of diagnosing the development of a disease associated with aberrant DNA methylation in a DNA-containing sample from a subject comprising:
   a) adding to the sample containing DNA from the subject, a plurality of copies of a plurality of synthetic polynucleotide standards (STDgenes), wherein each different STDgene is specific for a different TARGETgene of interest, wherein each different STDgene comprises a DNA sequence having a similar number of nucleotides as the TARGETgene for which it is specific, wherein each different STDgene has 5' and 3' end nucleotide sequences which are homologous to nucleotide sequences of the TARGETgene for which it is specific, wherein the intervening DNA sequence between the 5' and 3' ends of each different STDgene lacks homology to the sequence of the TARGETgene for which it is specific or other human DNA; and wherein at least two different STDgenes are added to the sample;
   b) isolating and processing the DNA in the sample of a) to prepare the DNA for methylation-specific PCR via bisulfite treatment;
   c) amplifying the DNA in b) with at least two different external methylation-independent PCR primer pairs, where each different primer pair is capable of selectively hybridizing to only one of the TARGETgenes of interest and also to the STDgene specific for that one TARGETgene, using PCR under conditions sufficient to produce a first amplification product;
   d) obtaining a diluted sample of the first amplification product of c);
   e) for each different TARGETgene of interest adding to d) one pair of internal methylation-dependent PCR primers specific for the TARGETgene of interest, one pair of internal PCR primers specific for the STDgene for the TARGETgene of interest, a unique optically detectable labeled DNA probe which specifically hybridizes to the TARGETgene of interest, and a unique optically detectable labeled DNA probe which specifically hybridizes to the STDgene for the TARGETgene of interest; and f) amplifying the DNA in e using quantitative real-time PCR under conditions sufficient to produce a second amplification product which provides quantification of the amount of copies of (i) the methylated TARGETgenes of interest and (ii) the STDgene for the TARGETgenes of interest, wherein an increase in the quantity of methylated copies of the TARGETgenes of interest obtained from the sample compared to a control is indicative, of an increased risk or presence of the disease; and g) diagnosing the subject as having an increased risk or presence of the disease.

10. The method of claim 9, wherein the disease is cancer, and the increase in the quantity of methylated copies of the TARGETgenes of interest obtained from the sample compared to control is indicative of oncogenic, cancerous, premalignant or metaplastic changes in the tissue of the subject.

11. The method of claim 9, wherein the sample obtained from the subject is selected from the group consisting of: blood, serum and plasma.

* * * * *

UNITED STATES PATENT AND TRADEMARK OFFICE
CERTIFICATE OF CORRECTION

PATENT NO. : 10,450,609 B2
APPLICATION NO. : 14/402434
DATED : October 22, 2019
INVENTOR(S) : Saraswati Sukumar et al.

Page 1 of 1

It is certified that error appears in the above-identified patent and that said Letters Patent is hereby corrected as shown below:

In the Specification

At Column 1, please replace Line numbers 19-22 with the following:
--This invention was made with government support under CA006973 awarded by the National Institutes of Health and W81XWH-04-1-0595 awarded by the Army Medical Research and Materiel Command. The government has certain rights in the invention.--

Signed and Sealed this
Seventh Day of July, 2020

Andrei Iancu
*Director of the United States Patent and Trademark Office*